US007413741B2

(12) United States Patent
Depraetere et al.

(10) Patent No.: US 7,413,741 B2
(45) Date of Patent: Aug. 19, 2008

(54) HCV E1 COMPRISING SPECIFIC DISULFIDE BRIDGES

(75) Inventors: Stany Depraetere, Oudenaarde (BE); Erik Depla, Destelbergen (BE); Gert Verheyden, Ghent (BE); Alfons Bosman, Opwijk (BE)

(73) Assignee: Innogenetics N.V., Ghent (BE)

( * ) Notice: Subject to any disclaimer, the term of this patent is extended or adjusted under 35 U.S.C. 154(b) by 736 days.

(21) Appl. No.: 11/073,942

(22) Filed: Mar. 8, 2005

(65) Prior Publication Data

US 2006/0034861 A1 Feb. 16, 2006

Related U.S. Application Data

(60) Provisional application No. 60/550,421, filed on Mar. 8, 2004.

(30) Foreign Application Priority Data

Mar. 9, 2004 (EP) .................................. 04447057

(51) Int. Cl.
*A61K 39/00* (2006.01)
*A61K 39/12* (2006.01)
*A61K 39/29* (2006.01)
*C12N 15/09* (2006.01)
*C12N 15/51* (2006.01)

(52) U.S. Cl. .................. 424/228.1; 435/69.1; 435/69.3; 424/184.1; 424/189.1; 424/192.1; 424/204.1

(58) Field of Classification Search ........................ None
See application file for complete search history.

(56) References Cited

U.S. PATENT DOCUMENTS

| 6,635,257 | B1 | 10/2003 | Depla |
| 7,101,561 | B2 | 9/2006 | Maertens |
| 2004/0126395 | A1 | 7/2004 | Maertens |
| 2004/0185061 | A1* | 9/2004 | Bosman et al. .......... 424/189.1 |

FOREIGN PATENT DOCUMENTS

| BE | WO 02/086101 | * 10/2002 |
| EP | WO 99/67285 | * 12/1999 |
| WO | WO 96/04301 | 2/1996 |
| WO | WO 98/50556 | 11/1998 |
| WO | WO 99/50301 | 10/1999 |
| WO | WO 02/085932 | 10/2002 |
| WO | WO 03/051912 | 6/2003 |

OTHER PUBLICATIONS

Berzofsky et al., "Progress on new vaccine strategies against chronic viral infections," The Journal of Clinical Investigation, vol. 114 No. 4, pp. 450-462 (Aug. 2004).*
LeRoux-Roels, Development of prophylactic and therapeutic vaccines against hepatitis C virus, Expert Review of Vaccines, vol. 4 No. 3, pp. 351-371 (Jun. 2005).*
Liang et al., "Pathogenesis, natural history, treatment, and prevention of hepatitis C," Annals of Internal Medicine, vol. 132 No. 4, pp. 296-305 (Feb. 2000).*
Rollier et al., "Control of Heterologous Hepatitis C Virus Infection in Chimpanzees Is Associated with the Quality of Vaccine-Induced Peripheral T-Helper Immune Response," Journal of Virology, vol. 78 No. 1, pp. 187-196 (Jan. 2004).*
Tan et al., "Strategies for hepatitis C therapeutic intervention: now and next,"Current Opinion in Phamacology, vol. 4 No. 5, pp. 465-470 (Oct. 2004).*
Lauer et al., "Vaccine-induced T-cell responses against HCV: one step taken, more to follow," Gastroenterology, vol. 132 No. 4, pp. 1626-1628 (2007).*
Merola et al. Folding of Hepatitis C Virus E1 Glycoprotein in a Cell Free System (2002) J Virol 75, 11205-11217.
Garry et al, Proteomics computational analyses suggest that hepatitis C virus E1 and pestivirus E2 envelope glycoproteins are truncated class II fusion proteins (2003) Virology 307, 255-265.
Partial European Search Report dated Aug. 27, 2004, issued in connection with EP 04 44 7057.
Sobolev et al, "Comparative analysis of amino acid sequences from envelope proteins isolated from different hepatitis C virus variants: possible role of conservative and variable regions", J. Viral Hepatitis 7, pp. 368-374 (2000).
Deleersnyder et al, "Formation of Native Hepatitis C Virus Glycoprotein Complexes", J. Virology 71, No. 1, pp. 697-704 (1997).
Hussy et al, "Purification and in vitro-phospholabeling of secretory envelope proteins E1 and E2 of hepatitis C Virus expressed in insect cells" Virus Research 45, pp. 45-57 (1996).

* cited by examiner

*Primary Examiner*—Zachariah Lucas
(74) *Attorney, Agent, or Firm*—Nixon & Vanderhye P.C.

(57) ABSTRACT

The invention relates to recombinantly or synthetically produced HCV E1 envelope proteins or parts thereof comprising disulfides between specific cysteine residues. The invention further relates to viral-like particles and compositions comprising said HCV E1 envelope proteins or parts thereof as well as to methods using said HCV E1 envelope proteins or parts thereof, and to kits comprising said HCV E1 envelope proteins or parts thereof.

9 Claims, 5 Drawing Sheets

Figure 1:
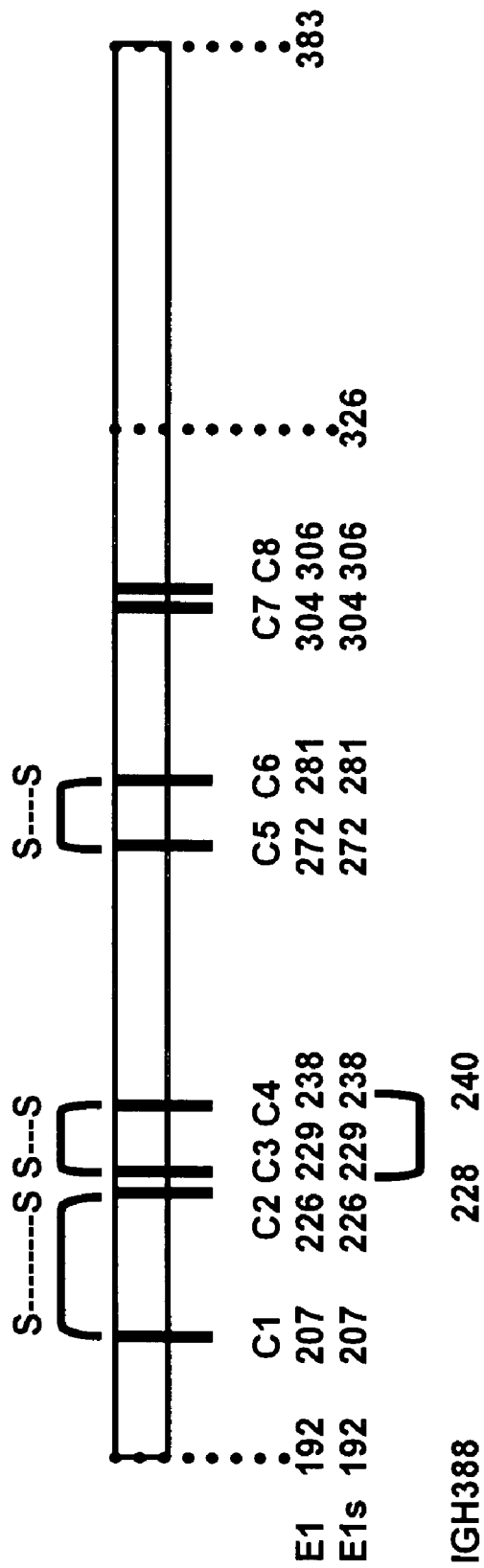

IGH 388 VH chain amino acid sequence (predicted CDR's are underlined; CDR = complementary determining region)

EEQLVESGGGPVKPGRSLRLSCAASGFTLSSYAINWVRQAPGQGLEWVSSISSSGSY
VSYADSVKGRFTISRDNAKNLVFLQLNSLRAGDTAVYRCTRDVNYYDTSEDYYGEAF
DIWGQGTMVTVSS (SEQ ID NO:19)

IGH 388 VKL chain amino acid sequence (predicted CDR's are underlined; CDR = complementary determining region)

DIQMTQSPSTLSAYVGDRVTITCRASQSVSRWLAWYQQRPGKAPKLLIYKASNLESG
VPSRFSGSGSGTEFTLTISSLQPDDFATYYCQQYKTYSNTFAQGTKLEIKR (SEQ
ID NO:20)

IGH 388 VH chain nucleic acid sequence

GAGGAGCAGTTGGTAGAGTCTGGGGGAGGCCCGGTCAAGCCTGGAAGGTCCCTGAGA
CTCTCCTGTGCAGCCTCTGGATTCACCCTCAGTAGTTATGCCATCAATTGGGTCCGC
CAGGCTCCAGGGCAGGGGCTGGAATGGGTCTCATCTATCAGTAGTAGTGGGAGTTAT
GTGTCCTACGCAGACTCGGTGAAGGGCCGCTTCACCATCTCCAGAGACAACGCCAAG
AACTTAGTGTTTCTGCAATTGAACAGCCTGAGAGCCGGCGACACGGCTGTTTATAGA
TGTACAAGAGATGTAAATTATTATGATACTAGTGAAGATTATTACGGTGAGGCTTTT
GATATCTGGGGCCAAGGGACAATGGTCACCGTCTCTTCA (SEQ ID NO:21)

IGH 388 VKL chain nucleic acid sequence

GACATCCAGATGACCCAGTCTCCTTCCACCCTGTCTGCATATGTAGGAGACAGAGTC
ACCATCACTTGCCGGGCCAGTCAGAGTGTTAGTCGCTGGTTGGCCTGGTATCAGCAA
AGACCAGGGAAAGCCCCCAAACTCCTGATCTATAAGGCGTCTAATTTAGAAAGTGGG
GTCCCATCAAGGTTCAGCGGCAGTGGATCTGGGACAGAATTCACTCTCACCATCAGC
AGCCTGCAGCCTGATGATTTTGCAACTTATTATTGCCAACAATATAAAACTTATTCT
AACACTTTTGCCCAGGGGACCAAGCTGGAGATCAAGCGA (SEQ ID NO:22)

FIGURE 4

SEQUENCE LISTING

```
<160> NUMBER OF SEQ ID NOS: 22

<210> SEQ ID NO 1
<211> LENGTH: 135
<212> TYPE: PRT
<213> ORGANISM: hepatitis C virus

<400> SEQUENCE: 1

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp
    130                 135

<210> SEQ ID NO 2
<211> LENGTH: 4
<212> TYPE: PRT
<213> ORGANISM: hepatitis C virus
```

-continued

```
<400> SEQUENCE: 2

Tyr Glu Val Arg
1

<210> SEQ ID NO 3
<211> LENGTH: 36
<212> TYPE: PRT
<213> ORGANISM: hepatitis C virus

<400> SEQUENCE: 3

Asp Val Ser Gly Met Tyr His Val Thr Asn Asp Cys Ser Asp Ser Ser
1               5                   10                  15

Ile Val Tyr Glu Ala Ala Asp Met Ile Met His Thr Pro Gly Cys Val
            20                  25                  30

Pro Cys Val Arg
        35

<210> SEQ ID NO 4
<211> LENGTH: 6
<212> TYPE: PRT
<213> ORGANISM: hepatitis C virus

<400> SEQUENCE: 4

Glu Asn Asp Ser Ser Arg
1               5

<210> SEQ ID NO 5
<211> LENGTH: 12
<212> TYPE: PRT
<213> ORGANISM: hepatitis C virus

<400> SEQUENCE: 5

Cys Trp Val Ala Leu Thr Pro Thr Leu Ala Ala Arg
1               5                   10

<210> SEQ ID NO 6
<211> LENGTH: 10
<212> TYPE: PRT
<213> ORGANISM: hepatitis C virus

<400> SEQUENCE: 6

Asp Ala Ser Val Pro Thr Thr Thr Ile Arg
1               5                   10

<210> SEQ ID NO 7
<211> LENGTH: 36
<212> TYPE: PRT
<213> ORGANISM: hepatitis C virus

<400> SEQUENCE: 7

His Val Asp Leu Leu Val Gly Ala Ala Ala Phe Cys Ser Ala Met Tyr
1               5                   10                  15

Val Gly Asp Leu Cys Gly Ser Val Phe Leu Val Ser Gln Leu Phe Thr
            20                  25                  30

Ile Ser Pro Arg
        35

<210> SEQ ID NO 8
<211> LENGTH: 20
<212> TYPE: PRT
<213> ORGANISM: hepatitis C virus

<400> SEQUENCE: 8
```

His Glu Thr Val Gln Asp Cys Asp Cys Ser Ile Tyr Pro Gly His Ile
1               5                   10                  15

Thr Gly His Arg
            20

<210> SEQ ID NO 9
<211> LENGTH: 15
<212> TYPE: PRT
<213> ORGANISM: hepatitis C virus

<400> SEQUENCE: 9

Met Ala Trp Asp Met Met Met Asn Trp His His His His His
1               5                   10                  15

<210> SEQ ID NO 10
<211> LENGTH: 20
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa 1 is an N-terminally acetylated serine
<220> FEATURE:
<221> NAME/KEY: MISC_FEATURE
<222> LOCATION: (20)..(20)
<223> OTHER INFORMATION: Xaa 20 is a C-terminally amidated serine

<400> SEQUENCE: 10

Xaa Gln Leu Phe Thr Ile Ser Pro Arg Arg His Glu Thr Val Gln Asp
1               5                   10                  15

Cys Asn Cys Xaa
            20

<210> SEQ ID NO 11
<211> LENGTH: 14
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa  is an N-terminally acetylated alanine
<220> FEATURE:
<221> NAME/KEY: MISC_FEATURE
<222> LOCATION: (14)..(14)
<223> OTHER INFORMATION: Xaa  is a C-terminally amidated serine

<400> SEQUENCE: 11

Xaa Phe Cys Ser Ala Met Tyr Val Gly Asp Leu Cys Gly Xaa
1               5                   10

<210> SEQ ID NO 12
<211> LENGTH: 24
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is an N-terminally acetylated  asparagine
<220> FEATURE:
<221> NAME/KEY: MISC_FEATURE
<222> LOCATION: (24)..(24)
<223> OTHER INFORMATION: Xaa is a C-terminally amidated proline

<400> SEQUENCE: 12

Xaa Asp Cys Ser Asn Ser Ser Ile Val Tyr Glu Ala Ala Asp Met Ile
1               5                   10                  15

Met His Thr Pro Gly Cys Val Xaa

-continued

```
<210> SEQ ID NO 13
<211> LENGTH: 20
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is an N-terminally acetylated proline
<220> FEATURE:
<221> NAME/KEY: MISC_FEATURE
<222> LOCATION: (20)..(20)
<223> OTHER INFORMATION: Xaa is a C-terminally amidated alanine

<400> SEQUENCE: 13

Xaa Cys Val Arg Glu Asn Asn Ser Ser Arg Cys Trp Val Ala Leu Thr
1               5                   10                  15

Pro Thr Leu Xaa
            20

<210> SEQ ID NO 14
<211> LENGTH: 38
<212> TYPE: PRT
<213> ORGANISM: hepatitis C virus
<220> FEATURE:
<221> NAME/KEY: MISC_FEATURE
<222> LOCATION: (38)..(38)
<223> OTHER INFORMATION: Xaa is a biotinylated and C-terminally amidated
      lysine

<400> SEQUENCE: 14

Tyr Glu Val Arg Asn Val Ser Gly Ile Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Gly Gly Xaa
        35

<210> SEQ ID NO 15
<211> LENGTH: 33
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is an N-terminally acetylated isoleucine
<220> FEATURE:
<221> NAME/KEY: MISC_FEATURE
<222> LOCATION: (31)..(31)
<223> OTHER INFORMATION: Xaa is a biotinylated lysine

<400> SEQUENCE: 15

Xaa Val Tyr Glu Ala Ala Asp Met Ile Met His Thr Pro Gly Cys Val
1               5                   10                  15

Pro Cys Val Arg Glu Asn Asn Ser Ser Arg Cys Trp Val Gly Xaa Gly
            20                  25                  30

Gly

<210> SEQ ID NO 16
<211> LENGTH: 14
<212> TYPE: PRT
<213> ORGANISM: hepatitis C virus

<400> SEQUENCE: 16

Ile Tyr Glu Ala Ala Asp Met Ile Met His Thr Pro Gly Cys
```

```
<210> SEQ ID NO 17
<211> LENGTH: 37
<212> TYPE: PRT
<213> ORGANISM: hepatitis C virus
<220> FEATURE:
<221> NAME/KEY: MISC_FEATURE
<222> LOCATION: (1)..(1)
<223> OTHER INFORMATION: Xaa is an N-terminally acetylated proline
<220> FEATURE:
<221> NAME/KEY: MISC_FEATURE
<222> LOCATION: (37)..(37)
<223> OTHER INFORMATION: Xaa is a biotinylated and C-terminally amidated
      lysine

<400> SEQUENCE: 17

Xaa Cys Val Arg Glu Asn Asn Ser Ser Arg Cys Trp Val Ala Leu Thr
1               5                   10                  15

Pro Thr Leu Ala Ala Arg Asn Ala Ser Val Pro Thr Thr Ile Arg
            20                  25                  30

Arg His Val Asp Xaa
        35

<210> SEQ ID NO 18
<211> LENGTH: 13
<212> TYPE: PRT
<213> ORGANISM: hepatitis C virus

<400> SEQUENCE: 18

Pro Cys Val Arg Glu Asn Asn Ser Ser Arg Cys Trp Val
1               5                   10

<210> SEQ ID NO 19
<211> LENGTH: 127
<212> TYPE: PRT
<213> ORGANISM: Homo sapiens

<400> SEQUENCE: 19

Glu Glu Gln Leu Val Glu Ser Gly Gly Gly Pro Val Lys Pro Gly Arg
1               5                   10                  15

Ser Leu Arg Leu Ser Cys Ala Ala Ser Gly Phe Thr Leu Ser Ser Tyr
            20                  25                  30

Ala Ile Asn Trp Val Arg Gln Ala Pro Gly Gln Gly Leu Glu Trp Val
        35                  40                  45

Ser Ser Ile Ser Ser Ser Gly Ser Tyr Val Ser Tyr Ala Asp Ser Val
    50                  55                  60

Lys Gly Arg Phe Thr Ile Ser Arg Asp Asn Ala Lys Asn Leu Val Phe
65                  70                  75                  80

Leu Gln Leu Asn Ser Leu Arg Ala Gly Asp Thr Ala Val Tyr Arg Cys
                85                  90                  95

Thr Arg Asp Val Asn Tyr Tyr Asp Thr Ser Glu Asp Tyr Tyr Gly Glu
            100                 105                 110

Ala Phe Asp Ile Trp Gly Gln Gly Thr Met Val Thr Val Ser Ser
        115                 120                 125

<210> SEQ ID NO 20
<211> LENGTH: 108
<212> TYPE: PRT
<213> ORGANISM: Homo sapiens

<400> SEQUENCE: 20
```

-continued

```
Asp Ile Gln Met Thr Gln Ser Pro Ser Thr Leu Ser Ala Tyr Val Gly
1               5                   10                  15

Asp Arg Val Thr Ile Thr Cys Arg Ala Ser Gln Ser Val Ser Arg Trp
            20                  25                  30

Leu Ala Trp Tyr Gln Gln Arg Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Thr Tyr Ser Asn
                85                  90                  95

Thr Phe Ala Gln Gly Thr Lys Leu Glu Ile Lys Arg
            100                 105

<210> SEQ ID NO 21
<211> LENGTH: 381
<212> TYPE: DNA
<213> ORGANISM: Homo sapiens

<400> SEQUENCE: 21
gaggagcagt tggtagagtc tgggggaggc ccggtcaagc ctggaaggtc cctgagactc      60
tcctgtgcag cctctggatt caccctcagt agttatgcca tcaattgggt ccgccaggct     120
ccagggcagg ggctggaatg ggtctcatct atcagtagta gtgggagtta tgtgtcctac     180
gcagactcgg tgaagggccg cttcaccatc tccagagaca acgccaagaa cttagtgttt     240
ctgcaattga acagcctgag agccggcgac acggctgttt atagatgtac aagagatgta     300
aattattatg atactagtga agattattac ggtgaggctt ttgatatctg gggccaaggg     360
acaatggtca ccgtctcttc a                                               381

<210> SEQ ID NO 22
<211> LENGTH: 324
<212> TYPE: DNA
<213> ORGANISM: Homo sapiens

<400> SEQUENCE: 22
gacatccaga tgacccagtc tccttccacc ctgtctgcat atgtaggaga cagagtcacc      60
atcacttgcc gggccagtca gagtgttagt cgctggttgg cctggtatca gcaaagacca     120
gggaaagccc ccaaactcct gatctataag gcgtctaatt tagaaagtgg ggtcccatca     180
aggttcagcg gcagtggatc tgggacagaa ttcactctca ccatcagcag cctgcagcct     240
gatgattttg caacttatta ttgccaacaa tataaaactt attctaacac ttttgcccag     300
gggaccaagc tggagatcaa gcga                                            324
```

HCV E1 COMPRISING SPECIFIC DISULFIDE BRIDGES

The present application is based on and claims benefit of EP Patent Application No. 04447057.3 filed on 9 Mar. 2004 and claims benefit to U.S. Provisional Application No. 60/550,421 filed on 8 Mar. 2004, the entire contents of each of which is hereby incorporated by reference.

FIELD OF THE INVENTION

The invention relates to recombinantly or synthetically produced HCV E1 envelope proteins or parts thereof comprising disulfides between specific cysteine residues. The invention further relates to viral-like particles and compositions comprising said HCV E1 envelope proteins or parts thereof as well as to methods using said HCV E1 envelope proteins or parts thereof, and to kits comprising said HCV E1 envelope proteins or parts thereof.

BACKGROUND OF THE INVENTION

The about 9.6 kb single-stranded RNA genome of the HCV virus comprises a 5'- and 3'-non-coding region (NCRs) and, in between these NCRs a single long open reading frame of about 9 kb encoding an HCV polyprotein of about 3000 amino acids.

HCV polypeptides are produced by translation from the open reading frame and cotranslational proteolytic processing. Structural proteins are derived from the amino-terminal one-fourth of the coding region and include the capsid or Core protein (about 21 kDa), the E1 envelope glycoprotein (about 35 kDa) and the E2 envelope glycoprotein (about 70 kDa, previously called NS1), and p7 (about 7 kDa). The E2 protein can occur with or without a C-terminal fusion of the p7 protein (Shimotohno et al. 1995). Recently, an alternative open reading frame in the Core-region was found which is encoding and expressing a protein of about 17 kDa called F (Frameshift) protein (Xu et al. 2001; Ou & Xu in U.S. Patent Application Publication No. US2002/0076415). In the same region, ORFs for other 14-17 kDa ARFPs (Alternative Reading Frame Proteins), A1 to A4, were discovered and antibodies to at least A1, A2 and A3 were detected in sera of chronically infected patients (Walewski et al. 2001). From the remainder of the HCV coding region, the non-structural HCV proteins are derived which include NS2 (about 23 kDa), NS3 (about 70 kDa), NS4A (about 8 kDa), NS4B (about 27 kDa), NS5A (about 58 kDa) and NS5B (about 68 kDa) (Grakoui et al. 1993).

HCV is the major cause of non-A, non-B hepatitis worldwide. Acute infection with HCV (20% of all acute hepatitis infections) frequently leads to chronic hepatitis (70% of all chronic hepatitis cases) and end-stage cirrhosis. It is estimated that up to 20% of HCV chronic carriers may develop cirrhosis over a time period of about 20 years and that of those with cirrhosis between 1 to 4%/year is at risk to develop liver carcinoma (Lauer & Walker 2001, Shiffman 1999). An option to increase the life-span of HCV-caused end-stage liver disease is liver transplantation (30% of all liver transplantations world-wide are due to HCV-infection).

It is generally accepted that the more a recombinantly expressed HCV envelope protein is resembling a naturally produced HCV envelope protein (naturally produced in the sense of being the consequence of infection of a host by HCV), the better such an HCV envelope protein is suited for diagnostic, prophylactic and/or therapeutic uses or purposes, and for use in drug screening methods. HCV envelope proteins are currently obtained via recombinant expression systems such as mammalian cell cultures infected with E1 or E2-recombinant vaccinia virus (see, e.g., WO96/04385), stably transformed mammalian cell lines, and recombinant yeast cells (see, e.g., WO02/086101). These expression systems suffer from the drawback that the expressed HCV envelope proteins tend to form aggregates that comprise contaminating proteins and which are in part stabilized by intermolecular disulfide bridges. In order to obtain sufficient amounts of recombinant HCV envelope proteins the bulk of intracellularly accumulated HCV envelope proteins is reduced and/or cysteines are blocked and/or a detergent is used during the purification process. As such the obtained recombinant HCV envelope proteins are not closely resembling naturally produced HCV envelope proteins.

Folding of the HCV E1 envelope protein is dependent on the formation of disulfide bridges. At present not much is known about the requirements needed for an HCV E1 envelope protein to assume its folding. It has been suggested that at least some of the cysteines of the HCV E1 envelope protein are involved in intramolecular disulfide bridges. In an in vitro assay it was shown that oxidation of HCV E1 (i.e., the formation of disulfides in HCV E1) requires the presence of both Core and E2 (Merola et al. 2001). Recently, the results of a computer prediction of the disulfide bridges within HCV E1 was published. Disulfides between the cysteine residues 207 and 306, 226 and 304, 229 and 281, and 238 and 272 were predicted (Garry and Dash 2003). Note that the HCV E1 amino acid sequences in FIG. 1 and FIG. 5 of this reference are not identical to each other and that the HCV E1 amino acid sequence in FIG. 1 is missing amino acid 250; the above-indicated numbering of the cysteine residues has been adapted relative to Garry and Dash (2003) to correspond to the numbering of the cysteine residues as used hereafter in the description of the invention.

SUMMARY OF THE INVENTION

The present invention relates in a first aspect to a recombinant or synthetic HCV E1 envelope protein or a part thereof comprising at least one, or two, or all of the following disulfides:

a disulfide between the pair of cysteines at amino acid positions 207 and 226, a disulfide between the pair of cysteines at amino acid positions 229 and 238, or a disulfide between the pair of cysteines at amino acid positions 272 and 281, wherein said amino acid positions are relative to the HCV polyprotein which is starting with the methionine of the Core protein at amino acid position 1 of said HCV polyprotein. Furthermore, said recombinant or synthetic HCV E1 envelope protein or a part thereof can further comprise at least one of the cysteines at amino acid positions 304 or 306 wherein said at least one cysteine is carrying a free thiol group or a thiol group which is blocked, i.e., reversibly or irreversibly blocked. Alternatively, said at least one cysteine at amino acid position 304 or 306 is mutated to a non-cysteine amino acid or is deleted.

In a further aspect of the invention any of the above HCV E1 envelope proteins or parts thereof is comprised in a viral-like particle.

The invention also relates to compositions comprising any of the above HCV E1 envelope protein or part thereof or a viral-like particle and at least one of a pharmaceutically acceptable carrier, adjuvant or vehicle. In particular said composition is an HCV vaccine, such as a prophylactic or therapeutic HCV vaccine The invention further embodies antibodies or fragments thereof selectively binding to an HCV E1 envelope protein or a part thereof comprising at least one, or two, or all of the following disulfides:
  a disulfide between the pair of cysteines at amino acid positions 207 and 226,
  a disulfide between the pair of cysteines at amino acid positions 229 and 238, or
  a disulfide between the pair of cysteines at amino acid positions 272 and 281, wherein said amino acid positions are relative to the HCV polyprotein which is starting with the methionine of the Core protein at amino acid position 1 of said HCV polyprotein;

or selectively binding to a viral-like particle comprising any of said HCV E1 envelope. proteins or parts thereof, antibodies capable of competing with said antibodies for selectively binding said HCV E1 envelope protein, or a fragment of any of said antibodies.

Said antibodies can be isolated from a mammal immunized with any of the above HCV E1 envelope proteins or parts thereof or with the above viral-like particle. Fragments of said antibodies can than be prepared. In particular said antibody or fragment thereof is a monoclonal antibody or a fragment thereof. A specific antibody is the antibody secreted by the hybridoma cell line of DSM deposit with accession number ACC 2470. Again, fragments of this specific antibody can than be prepared. Determining if two antibodies are competing with each other for binding an epitope can easily be performed.

The invention also relates to the hybridoma cell line of DSM deposit with accession number ACC 2470.

Methods for determining the presence of HCV antibodies in a sample are part of another embodiment of the invention, said methods comprising the steps of:
(i) contacting said sample with any of the above HCV E1 envelope proteins or parts thereof or with the above viral-like particle under conditions allowing the formation of an immunological antigen-antibody complex;
(ii) determining the immunological complex formed in (i);
(iii) inferring from (ii) the presence of HCV antibodies in said sample.

Methods for determining the presence of HCV E1 antigens in a sample are part of another embodiment of the invention, said methods comprising the steps of:
(i) contacting said sample with any of the above antibodies under conditions allowing the formation of an immunological antigen-antibody complex;
(ii) determining the immunological complex formed in (i);
(iii) inferring from (ii) the presence of HCV E1 antigens in said sample.

In particular, in step (i) of said methods any of the above HCV E1 envelope proteins or parts thereof, the above viral-like particle or any of the above antibodies is added as competitor; and said HCV E1 envelope protein or part thereof, viral-like particle or antibody used in said step (i) or said HCV E1 envelope protein or part thereof, viral-like particle or antibody added as competitor are labeled.

Another aspect of the invention relates to methods for screening compounds capable of modulating the binding between an HCV E1 envelope protein and an E1 ligand, said methods comprising:

(i) contacting said E1 ligand with any of the above HCV E1 envelope proteins or parts thereof with the above viral-like particle under conditions allowing the formation of an HCV E1-E1 ligand complex;
(ii) adding a compound suspected of modulating the binding between an HCV E1 envelope protein and an E1 ligand to the HCV E1-E1 ligand complex formed in (i);
(iii) determining the change in amount of HCV E1-E1 ligand complex formed in (i) and (ii);
(iv) inferring from (iii) whether the compound added in (ii) is a modulator of binding between an HCV E1 envelope protein and an E1 ligand.

Further methods for screening compounds capable of modulating the binding between an HCV E1 envelope protein and an E1 ligand, comprise the steps of:
(i) contacting, under conditions allowing the formation of an HCV E1-E1 ligand complex, said E1 ligand with any of the above HCV E1 envelope proteins or parts thereof or with the above viral-like particle in the presence and absence, respectively, of a compound suspected of modulating the binding between an HCV E1 envelope protein and an E1 ligand;
(ii) determining the amount of HCV E1-E1 ligand complex formed in (i) in the presence and absence of said compound;
(iii) inferring from (ii) whether said compound is a modulator of binding between an HCV E1 envelope protein and an E1 ligand.

In particular, in steps (i) of said methods any of above HCV E1 envelope proteins or parts thereof or the above viral-like particle is added as competitor; and said HCV E1 envelope protein or part thereof or viral-like particle used in said step (i) or said HCV E1 envelope protein or part thereof or viral-like particle added as competitor are labeled.

The invention additionally relates to diagnostic kits for determining the presence of HCV antibodies or HCV E1 envelope proteins in a sample, said kits comprising any of the above HCV E1 envelope proteins or parts, the above viral-like particle and/or any of the above antibodies.

Another aspect of the invention envisages methods of producing a recombinant HCV E1 envelope protein or part thereof according to the invention, said methods comprising the steps of
(i) expressing of an HCV E1 envelope protein or part thereof in a eukaryotic host;
(ii) isolating from the pool of HCV E1 envelope protein or part thereof expressed in (i) the non-aggregated monomeric fraction of HCV E1 envelope protein or part thereof according to the invention.

Methods of producing a synthetic HCV E1 envelope protein or part thereof according to the invention are part of a further aspect wherein said methods comprise:
(i) chemical synthesis of an HCV E1 envelope protein or part thereof;
(ii) introducing during or after the chemical synthesis of an HCV E1 envelope protein or part thereof at least one disulfide as determined in the current invention.

Yet another aspect of the invention relates to the use of any of the above HCV E1 envelope proteins or parts thereof the above viral-like particle and/or any of the above antibodies for the preparation of a medicament or a vaccine or for the preparation of an immunoassay or a diagnostic kit.

The use of any of the above HCV E1 envelope proteins or parts thereof or the above viral-like particle as a carrier of another protein or of a non-proteinaceous molecule form a further aspect of the invention.

In another aspect, the invention covers isolated proteins comprising an HCV E1 envelope protein or part thereof according to the invention. In particular said isolated protein is further comprising at least one of:
- an N-terminal flanking amino acid or amino acid sequence of an HCV protein or part thereof not naturally contiguous with said HCV E1 envelope protein or part thereof;
- a C-terminal flanking amino acid or amino acid sequence of an HCV protein or part thereof not naturally contiguous with said HCV E1 envelope protein or part thereof;
- an N-terminal flanking non-HCV amino acid or amino acid sequence;
- a C-terminal flanking non-HCV amino acid or amino acid sequence.

Alternatively, said isolated protein is comprising the HCV E1 envelope protein or part thereof as carrier protein.

FIGURE LEGENDS

FIG. 1. Schematic representation of a full-length HCV E1 envelope protein with indication of the relative position of the 8 cysteine residues numbered C1 to C8. The arabic numbers refer to amino acid positions in the HCV polyprotein and indicate the positions of the amino- and carboxy-terminal amino acids of a full-length HCV E1 envelope protein and the E1s protein (192 and 383 for E1, 192 and 326 for E1s, respectively; dotted lines) and the positions of said 8 cysteine residues. The indicated intramolecular disulfide bridges ("S—S") were determined as outlined in the Examples. Further indicated is the relative position of the epitope selectively recognized by the antibody 1GH388 (see also FIG. 5 and Legend thereto).

Figure 2:
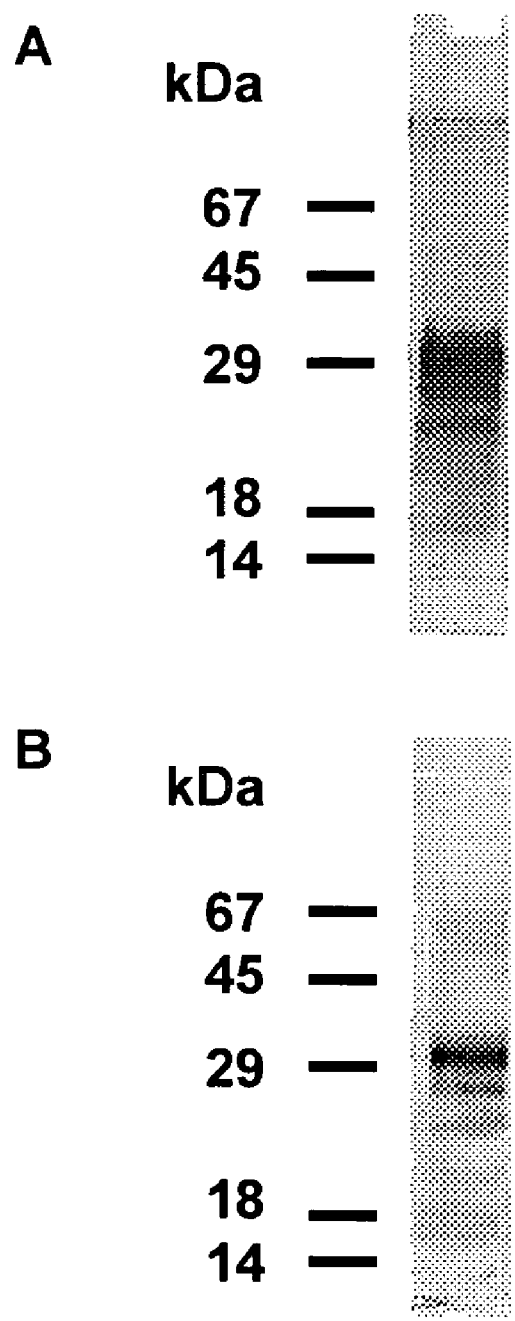

FIG. 2. Non-reducing SDS-PAGE followed by silver staining (A) and western blotting (B) of the E1s viral-like particles obtained as described in Example 1. To the left are indicated the molecular weights of the molecular weigt markers.

Figure 3:
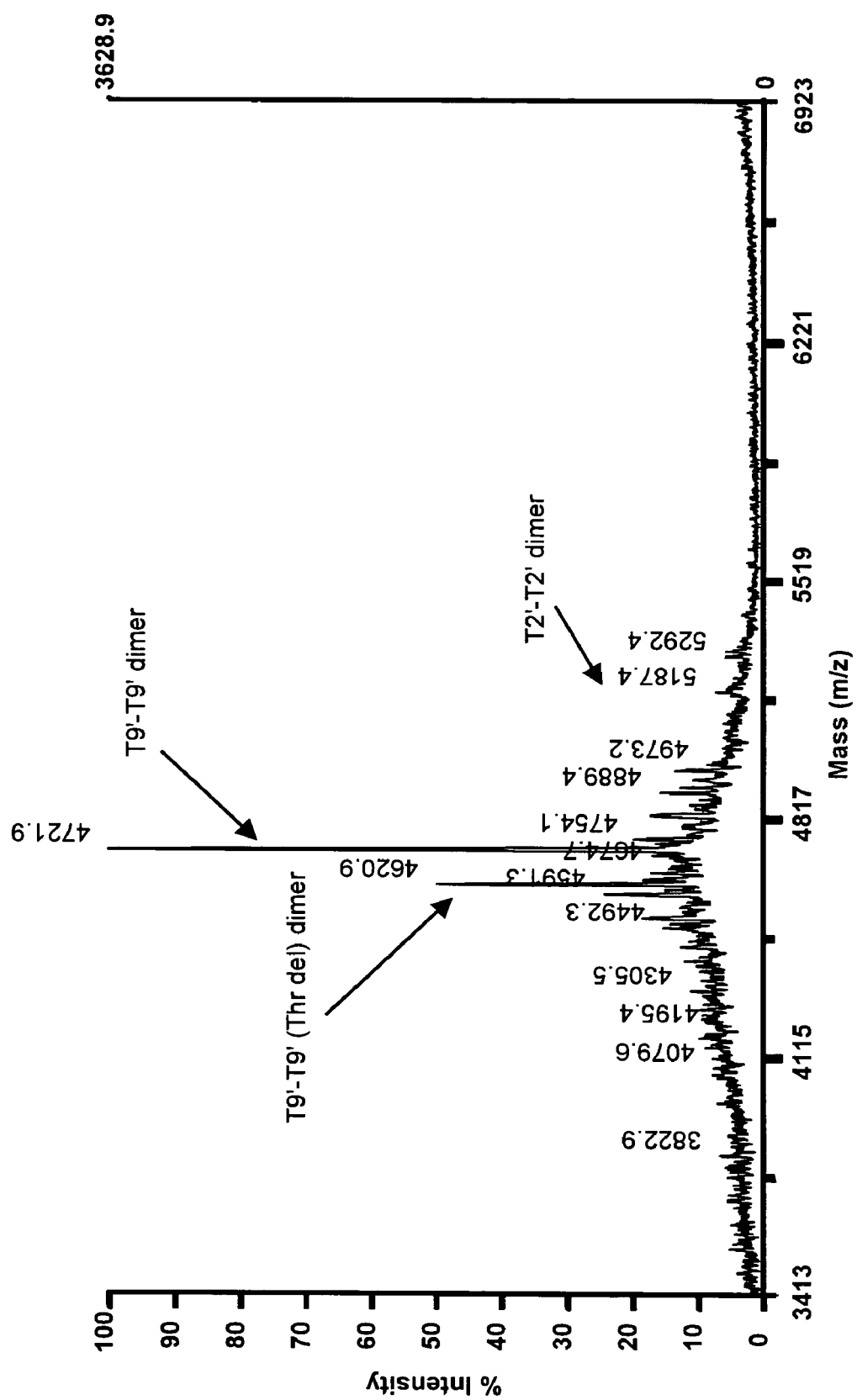

FIG. 3. Mid-range (3-10 kDa) MALDI-TOF-MS spectrum of T2'- T7'-T9' peptide mixture left to oxidize for 31 h as described in Example 5. T9' (Thr del) represents the side product of T9' formed during peptide synthesis and which lacks one of the two threonine-residues compared to T9.

FIG. 4. Amino acid sequences and nucleic acid sequences of the VH and VKL chains of the monoclonal antibody IGH388 obtained and characterized as described in Examples 7 and 8 hereafter.

Figure 5:
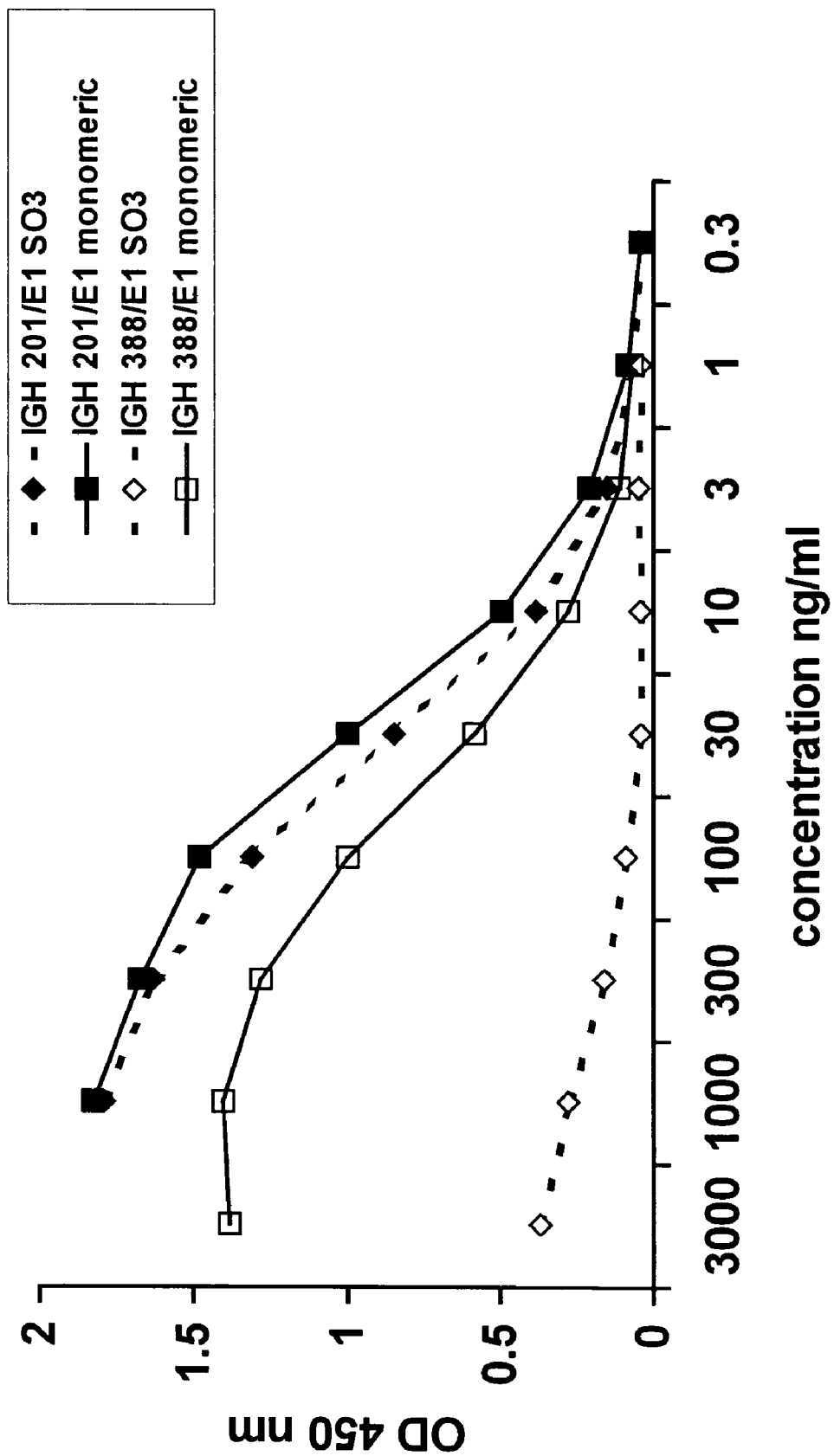

FIG. 5. Binding of the monoclonal antibodies IGH 201 and IGH 388 with monomeric E1 or sulphonated E1 ("E1 SO3") expressed as optical density measured in ELISA. Monomeric E1 or sulphonated E1 ("E1 SO3") was coated on ELISA plates at a concentration of 2 µg/mL. After blocking a serial dilution of the antibodies was incubated, the starting concentration for IGH 201 was 1 µg/mL, for IGH 388 3 µg/mL. The dilution factor applied is about 3.16 fold. Finally after washing bound antibodies are detected using an anti-mouse or anti-human secondary antiserum conjugated with peroxidase.

DETAILED DESCRIPTION OF THE INVENTION

The terms "protein", "polypeptide" and "peptide" are used interchangeably herein. Likewise, the terms "disulfide", "disulfide bond" and "disulfide bridge" are used interchangeably herein.

In work leading to the present invention a non-aggregated monomeric HCV E1 envelope protein fraction was isolated from the bulk of recombinantly expressed HCV E1 envelope protein in the absence of a reducing agent (see Example 1; see Example 1 also for a description of monomeric HCV E1 envelope protein). Due to the omission of conditions disrupting intra- and intermolecular disulfides during purification this monomeric recombinant HCV E1 envelope protein is believed to advantageously resemble naturally produced HCV E1 envelope protein.

A first surprising observation was that the obtained non-aggregated monomeric HCV E1 envelope protein fraction contained intramolecular disulfide bonds. This is in contradiction with the report by Merola et al. (2002) who showed that both the HCV Core and E2 proteins assist the HCV E1 protein in its folding and oxidation. The results of the present invention indicate that no other HCV protein was required for formation of intramolecular disulfide bonds in the HCV E1 envelope protein. It is thus possible to obtain oxidized HCV E1 envelope protein closely resembling naturally produced HCV E1 envelope protein in a production and purification process not involving other HCV proteins such as Core and/or E2.

A second surprising aspect emerged after determining the position of the disulfide bonds in the obtained non-aggregated monomeric HCV E1 envelope protein fraction, i.e., after determining which cysteines of the HCV E1 envelope protein are involved in which disulfide bonds. The experimentally determined position of the disulfide bonds is completely different from the disulfide pattern predicted by Garry and Dash (2003). Furthermore surprising is that two of the eight cysteines in the non-aggregated monomeric HCV E1 envelope protein fraction of the invention are not engaged in intramolecular disulfide bonds.

In a first aspect the invention relates to a recombinant or synthetic HCV E1 envelope protein or a part thereof comprising at least one, or two, or all of the following disulfides:
- a disulfide between the pair of cysteines at amino acid positions 207 and 226,
- a disulfide between the pair of cysteines at amino acid positions 229 and 238, or
- a disulfide between the pair of cysteines at amino acid positions 272 and 281, wherein said amino acid positions are relative to the HCV polyprotein which is starting with the methionine of the Core protein at amino acid position 1 of said HCV polyprotein.

The amino acid positions indicated above are to be considered as relative: a skilled person will recognize that the numbering of the cysteines of the HCV E1 envelope protein in the HCV polyprotein can be subject of changes. Such changes in amino acid numbering can be the consequence of HCV genotype-, HCV subtype-, or HCV isolate-specific amino acid insertions, deletions or mutations in the Core and/or E1 portion of the HCV polyprotein. It is clear that said changes in amino acid numbering are relative to the amino acid numbering of the HCV E1 envelope protein as indicated in FIG. 1. In relation to the first aspect of the invention it is furthermore clear that any fragment of said HCV E1 envelope protein has to comprise at least one pair, or two pairs, or all three pairs of cysteines that can engage in the formation of a disulfide bond.

To further clarify the scope of the HCV E1 envelope protein variants envisaged by the current invention it is clear that any of the above HCV E1 envelope proteins of the invention can further comprise at least one of the cysteines at positions 304 and 306, i.e., the cysteines of the HCV E1 envelope protein not involved in an intramolecular disulfide bond. This at least one cysteine at position 304 or 306 can be the naturally occurring cysteine which is carrying a free thiol group or which is carrying a thiol group that is blocked. Alternatively, this at least one cysteine at position 304 or 306 is mutated to a non-cysteine amino acid or is deleted from the HCV E1 envelope protein.

The mutation of a cysteine to a non-cysteine amino acid can be conservative (e.g., to alanine or to serine) or non-conservative. A conservative substitution will in general affect the overall functioning of the protein wherein the substitution is introduced less seriously than a non-conservative substitution.

HCV E1 Envelope Protein

The HCV E1 envelope protein or part or variant thereof according to the invention may be of synthetic origin, i.e. synthesized by applying organic chemistry, or of recombinant origin. As "HCV E1 envelope protein" is herein understood any isolated HCV E1 envelope protein or any part thereof comprising at least one, or two, or three cysteine pairs as outlined above or comprising all of the three cysteine pairs as outlined above.

An HCV E1 envelope protein may be produced by expression in, e.g., mammalian or insect cells infected with recombinant viruses, yeast cells or bacterial cells.

More particularly, said mammalian cells include HeLa cells, Vero cells, RK13 cells, MRC-5 cells, Chinese hamster ovary (CHO) cells, Baby hamster kidney (BHK) cells and PK15 cells.

More particularly, said insect cells include cells of *Spodoptera frugiperda*, such as Sf9 cells.

More particularly, said recombinant viruses include recombinant vaccinia viruses, recombinant adenoviruses, recombinant baculoviruses, recombinant canary pox viruses, recombinant Semlike Forest viruses, recombinant alphaviruses, recombinant Ankara Modified viruses and recombinant avipox viruses.

More particularly, said yeast cells include cells of *Saccharomyces*, such as *Saccharomyces cerevisiae, Saccharomyces kluyveri*, or *Saccharomyces uvarum, Schizosaccharomyces*, such as *Schizosaccharomyces pombe, Kluyveromyces*, such as *Kluyveromyces lactis, Yarrowia*, such as *Yarrowia lipolytica, Hansenula*, such as *Hansenula polymorpha, Pichia*, such as *Pichia pastoris, Aspergillus* species, *Neurospora*, such as *Neurospora crassa*, or *Schwanniomyces*, such as *Schwanniomyces occidentalis*, or mutant cells derived from any thereof. More specifically, the HCV peptide or part thereof according to the invention is the product of expression in a *Hansenula* cell.

More particularly, said bacterial cells include cells of *Escherichia coli* or *Streptomyces* species.

Blocking of Cysteines

The cysteines in the above-defined E1 protein or parts thereof may be engaged in intramolecular disulfide bonds (said E1 protein is then also referred to as "oxidized E1") or may be blocked, e.g., by sulphonation (said E1 proteins is then also referred to as "sulphonated E1") or alkylation (said E1 proteins is then also referred to as "alkylated E1"). Alternatively the cysteines in said E1 protein are free, i.e., carry a free thiol-group (said E1 proteins is then referred to as "reduced E1"). Blocking of cysteines is outlined in more detail below.

An "irreversibly blocked cysteine" is a cysteine of which the cysteine thiol-group is irreversibly protected by chemical means. In particular, "irreversible protection" or "irreversible blocking" by chemical means refers to alkylation, preferably alkylation of a cysteine in a protein by means of alkylating agents, such as, for example, active halogens, ethylenimine or N-(iodoethyl)trifluoro-acetamide. In this respect, it is to be understood that alkylation of cysteine thiol-groups refers to the replacement of the thiol-hydrogen by $(CH_2)_nR$, in which n is 0, 1, 2, 3 or 4 and R=H, COOH, $NH_2$, $CONH_2$, phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine.

A "reversibly blocked cysteine" is a cysteine of which the cysteine thiol-groups is reversibly protected. In particular, the term "reversible protection" or "reversible blocking" as used herein contemplates covalently binding of modification agents to the cysteine thiol-groups, as well as manipulating the environment of the protein such, that the redox state of the cysteine thiol-groups remains (shielding). Reversible protection of the cysteine thiol-groups can be carried out chemically or enzymatically.

The term "reversible protection by enzymatical means" as used herein contemplates reversible protection mediated by enzymes, such as for example acyl-transferases, e.g. acyl-transferases that are involved in catalysing thio-esterification, such as palmitoyl acyltransferase.

The term "reversible protection by chemical means" as used herein contemplates reversible protection:

1. by modification agents that reversibly modify cysteinyls such as for example by sulphonation and thio-esterification;
2. by modification agents that reversibly modify the cysteinyls of the present invention such as, for example, by heavy metals, in particular $Zn^{2+}$, $Cd^{2+}$, mono-, dithio- and disulfide- compounds (e.g. aryl- and alkylmethanethiosulfonate, dithiopyridine, dithiomorpholine, dihydrolipoamide, Ellmann reagent, aldrothiol™ (Aldrich) (Rein et al. 1996), dithiocarbamates), or thiolation agents (e.g. gluthathion, N-Acetyl cysteine, cysteineamine). Dithiocarbamate comprise a broad class of molecules possessing an $R_1R_2NC(S)SR_3$ functional group, which gives them the ability to react with sulphydryl groups. Thiol containing compounds are preferentially used in a concentration of 0.1-50 mM, more preferentially in a concentration of 1-50 mM, and even more preferentially in a concentration of 10-50 mM;
3. by the presence of modification agents that preserve the thiol status (stabilise), in particular antioxidantia, such as for example DTT, dihydroascorbate, vitamins and derivates, mannitol, amino acids, peptides and derivates (e.g. histidine, ergothioneine, carnosine, methionine), gallates, hydroxyanisole, hydoxytoluene, hydroquinon, hydroxymethylphenol and their derivates in concentration range of 10 μM-10 mM, more preferentially in a concentration of 1-10 mM;
4. by thiol stabilising conditions such as, for example, (i) cofactors as metal ions ($Zn^{2+}$, $Mg^{2+}$), ATP, (ii) pH control (e.g. for proteins in most cases pH 5 or pH is preferentially thiol p$K_a$-2; e.g. for peptides purified by Reversed Phase Chromatography at pH ~2).

Combinations of reversible protection as described in (1), (2), (3) and (4) may be applied.

The reversible protection and thiol stabilizing compounds may be presented under a monomeric, polymeric or liposomic form.

The removal of the reversible protection state of the cysteine residues can be accomplished chemically or enzymatically by, e.g.:

a reductant, in particular DTT, DTE, 2-mercaptoethanol, dithionite, $SnCl_2$, sodium borohydride, hydroxylamine, TCEP, in particular in a concentration of 1-200 mM, more preferentially in a concentration of 50-200 mM;

removal of the thiol stabilising conditions or agents by e.g. pH increase;

enzymes, in particular thioesterases, glutaredoxine, thioredoxine, in particular in a concentration of 0.01-5 μM, even more particular in a concentration range of 0.1-5 μM.; or combinations of the above described chemical and/or enzymatical conditions.

The removal of the reversible protection state of the cysteine residues can be carried out in vitro or in vivo, e.g., in a cell or in an individual.

Viral-like Particles

In a further aspect of the invention any of the above HCV E1 envelope proteins or parts thereof is comprised in a viral-like particle.

The terms "oligomeric particle", "virus-like particle", "viral-like particle", or "VLP" are used interchangeably herein and are defined as structures of a specific nature and shape containing several HCV E1 envelope proteins. In particular these VLPs are not formed in cells but are reconstituted in vitro starting from purified HCV envelope proteins (see Example 1 of WO99/67285). It should be clear that the particles are defined to be devoid of infectious HCV RNA genomes. The particles can be higher-order particles of spherical nature which can be empty, consisting of a shell of envelope proteins in which lipids, detergents, the HCV core protein, or adjuvant molecules can be incorporated. The latter particles can also be encapsulated by liposomes or apolipoproteins, such as, for example, apolipoprotein B or low density lipoproteins, or by any other means of targeting said particles to a specific organ or tissue. In this case, such empty spherical particles are often referred to as "virus-like particles" or VLPs. Alternatively, the higher-order particles can be solid spherical structures, in which the complete sphere consists of HCV envelope protein oligomers, in which lipids, detergents, the HCV core protein, or adjuvant molecules can be additionally incorporated, or which in turn may be themselves encapsulated by liposomes or apolipoproteins, such as, for example, apolipoprotein B, low density lipoproteins, or by any other means of targeting said particles to a specific organ or tissue, e.g. asialoglycoproteins. The particles can also consist of smaller structures (compared to the empty or solid spherical structures indicated above) which are usually round-shaped and which usually do not contain more than a single layer of HCV envelope proteins. A typical example of such smaller particles are rosette-like structures. Such rosette-like structures are usually organized in a plane and are round-shaped, e.g. in the form of a wheel. Again lipids, detergents, the HCV core protein, or adjuvant molecules can be additionally incorporated, or the smaller particles may be encapsulated by liposomes or apolipoproteins, such as, for example, apolipoprotein B or low density lipoproteins, or by any other means of targeting said particles to a specific organ or tissue. Smaller particles may also form small spherical or globular structures consisting of a similar smaller number of HCV envelope proteins in which lipids, detergents, the HCV core protein, or adjuvant molecules could be additionally incorporated, or which in turn may be encapsulated by liposomes or apolipoproteins, such as, for example, apolipoprotein B or low density lipoproteins, or by any other means of targeting said particles to a specific organ or tissue. The size (i.e. the diameter) of the above-defined particles, as measured by dynamic light scattering (DLS) or electron microscope (EM) techniques, is usually between 1 to 100 nm, or between 2 to 70 nm. Virus-like particles of HCV envelope proteins have been described in International Patent Application Publication Nos. WO99/67285, WO02/055548 and in International Patent Publication No. WO02/086101. The HCV viral-like particles as described above can comprise HCV E1 envelope proteins or parts thereof according to the invention and can furthermore comprise other HCV E1 envelope proteins (e.g., from different HCV genotypes, -subtypes, or -isolates) and/or HCV E2 envelope proteins or parts thereof (see Examples 11 and 12 of WO99/67285).

Vaccines and Vaccine Compositions

The invention also relates to compositions comprising any of the above HCV E1 envelope protein or part thereof or the above-said viral-like particle and at least one of a pharmaceutically acceptable carrier, adjuvant or vehicle. In particular said composition is an HCV vaccine, such as a prophylactic or therapeutic HCV vaccine A vaccine or vaccine composition is an immunogenic composition capable of eliciting an immune response sufficiently broad and vigorous to provoke one or both of:

a stabilizing effect on the multiplication of a pathogen already present in a host and against which the vaccine composition is targeted; and an increase of the rate at which a pathogen newly introduced in a host, after immunization with a vaccine composition targeted against said pathogen, is resolved from said host.

A vaccine composition may also provoke an immune response broad and strong enough to exert a negative effect on the survival of a pathogen already present in a host or broad and strong enough to prevent an immunized host from developing disease symptoms caused by a newly introduced pathogen. A vaccine composition may also induce an immune response in a host already infected with the pathogen against which the immune response leading to a halting or reversion of disease progression in the absence of eradication of the pathogen. In particular the vaccine composition of the invention is a HCV vaccine composition. The HCV vaccine composition is comprising as active substance at least one HCV E1 envelope protein or part thereof according to the invention, or a VLP comprising said protein. In particular the HCV vaccine or HCV vaccine composition is comprising an effective amount of said HCV E1 envelope protein and/or of said VLP. Said HCV vaccine composition may additionally comprise one or more further active substances and/or at least one of a pharmaceutically acceptable carrier, adjuvant or vehicle.

An effective amount of an antigen (either "free" or in the form of a VLP) in a vaccine or vaccine composition is referred to as an amount of antigen required and sufficient to elicit an immune response. It will be clear to the skilled artisan that the immune response sufficiently broad and vigorous to provoke the effects envisaged by the vaccine composition may require successive (in time) immunizations with the vaccine composition as part of a vaccination scheme or vaccination schedule. The "effective amount" may vary depending on the health and physical condition of the individual to be treated, the age of the individual to be treated (e.g. dosing for infants may be lower than for adults) the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting pathogen and other relevant factors. It is expected that the effective antigen amount will fall in a relativelny broad range that can be determined through routine trials. Usually, the antigen amount will vary from 0.01 to 1000 µg/dose, more particularly from 0.1 to 100 µg/dose. Dosage treatment may be a single dose schedule or a multiple dose schedule. The vaccine may be administered in conjunction with other immunoregulatory agents.

A vaccine composition may comprise more than one antigen, i.e., a plurality of antigens, e.g. 2, 3, 4, 5, 6, 7, 8, 9, 10 or more, e.g., up to 15, 20, 25, 30, 40 or 50 or more distinct antigens. In particular, the HCV vaccine composition comprises as antigen(s) the HCV E1 envelope protein(s) or part(s) thereof according to the invention, or comprises VLPs comprising said HCV E1 envelope proteins. The vaccine can be "monotypic" wherein the HCV E1 antigens all are derived from the same HCV genotype, HCV subtype or HCV isolate. The vaccine can also be "polytypic" by comprising HCV E1 antigens derived from different (at least 2) HCV genotypes, HCV subtypes or HCV isolates.

Carriers, Adjuvants and Vehicles

A "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvantia typically comprise one or more of the compounds included in the following non-exhaustive list:

- large slowly metabolized macromolecules such as proteins, polysaccharides, polylactic acids, polyglycolic acids, polymeric amino acids, amino acid copolymers and inactive virus particles;
- aluminium hydroxide, aluminium phosphate (see International Patent Application Publication No. WO93/24148), alum ($KAl(SO_4)_2.12H_2O$), or one of these in combination with 3-0-deacylated monophosphoryl lipid A (see International Patent Application Publication No. WO93/19780);
- N-acetyl-muramyl-L-threonyl-D-isoglutamine (see U.S. Pat. No. 4,606,918), N-acetyl-normuramyl-L-alanyl-D-isoglutamine, N-acetylmuramyl-L-alanyl-D-isoglutamyl-L-alanine2-(1',2'-dipalmitoyl-sn-glycero-3-hydroxyphosphoryloxy)ethylamine;
- RIBI (ImmunoChem Research Inc., Hamilton, Mont., USA) which contains monophosphoryl lipid A (i.e., a detoxified endotoxin), trehalose-6,6-dimycolate, and cell wall skeleton (MPL+TDM+CWS) in a 2% squalene/Tween 80 emulsion. Any of the three components MPL, TDM or CWS may also be used alone or combined 2 by 2;
- adjuvants such as Stimulon (Cambridge Bioscience, Worcester, Mass., USA), SAF-1 (Syntex);
- adjuvants such as combinations between QS21 and 3-de-O-acetylated monophosphoryl lipid A (see International Patent Application Publication No. WO94/00153) which may be further supplemented with an oil-in-water emulsion (see, e.g., International Patent Application Publication Nos. WO95/17210, WO97/01640 and WO9856414) in which the oil-in-water emulsion comprises a metabolisable oil and a saponin, or a metabolisable oil, a saponin, and a sterol, or which may be further supplemented with a cytokine (see International Patent Application Publication No. WO98/57659);
- adjuvants such as MF-59 (Chiron), or poly[di(carboxylatophenoxy) phosphazene] based adjuvants (Virus Research Institute);
- blockcopolymer based adjuvants such as Optivax (Vaxcel, Cytrx) or inulin-based adjuvants, such as Algammulin and GammaInulin (Anutech);
- Complete or Incomplete Freund's Adjuvant (CFA or IFA, respectively) or Gerbu preparations (Gerbu Biotechnik). It is to be understood that Complete Freund's Adjuvant (CFA) may be used for non-human applications and research purposes as well;
- a saponin such as QuilA, a purified saponin such as QS21, QS7 or QS17, β-escin or digitonin;
- immunostimulatory oligonucleotides comprising unmethylated CpG dinucleotides such as [purine-purine-CG-pyrimidine-pyrimidine]oligonucleotides. These immunostimulatory oligonucleotides include CpG class A, B, and C molecules (Coley Pharmaceuticals), ISS (Dynavax), Immunomers (Hybridon). Immunostimulatory oligonucleotides may also be combined with cationic peptides as described, e.g., by Riedl et al. (2002);
- Immune Stimulating Complexes comprising saponins, for example Quil A (ISCOMS);
- excipients and diluents, which are inherently non-toxic and non-therapeutic, such as water, saline, glycerol, ethanol, wetting or emulsifying agents, pH buffering substances, preservatives, and the like;
- a biodegradable and/or biocompatible oil such as squalane, squalene, eicosane, tetratetracontane, glycerol, peanut oil, vegetable oil, in a concentration of, e.g., 1 to 10% or 2.5 to 5%;
- vitamins such as vitamin C (ascorbic acid or its salts or esters), vitamin E (tocopherol), or vitamin A;
- carotenoids, or natural or synthetic flavanoids;
- trace elements, such as selenium;
- any Toll-like receptor ligand as reviewed in Barton and Medzhitov (2002).

Any of the afore-mentioned adjuvants comprising 3-de-O-acetylated monophosphoryl lipid A, said 3-de-O-acetylated monophosphoryl lipid A may be forming a small particle (see International Patent Application Publication No. WO94/21292).

In any of the aforementioned adjuvants MPL or 3-de-O-acetylated monophosphoryl lipid A can be replaced by a synthetic analogue referred to as RC-529 or by any other amino-alkyl glucosaminide 4-phosphate (Johnson et al. 1999, Persing et al. 2002). Alternatively it can be replaced by other lipid A analogues such as OM-197 (Byl et al. 2003).

A "pharmaceutically acceptable vehicle" includes vehicles such as water, saline, physiological salt solutions, glycerol, ethanol, etc. Auxiliary substances such as wetting or emulsifying agents, pH buffering substances, preservatives may be included in such vehicles.

Typically, a vaccine or vaccine composition is prepared as an injectable, either as a liquid solution or suspension. Injection may be subcutaneous, intramuscular, intravenous, intraperitoneal, intrathecal, intradermal, intraepidermal. Other types of administration comprise implantation, suppositories, oral ingestion, enteric application, inhalation, aerosolization or nasal spray or drops. Solid forms, suitable for dissolving in, or suspension in, liquid vehicles prior to injection may also be prepared. The preparation may also be emulsified or encapsulated in liposomes for enhancing adjuvant effect.

Antibodies

The invention further embodies antibodies selectively binding to an HCV E1 envelope protein or a part thereof comprising at least one, or two, or all of the following disulfides:

a disulfide between the pair of cysteines at amino acid positions 207 and 226, a disulfide between the pair of cysteines at amino acid positions 229 and 238, or a disulfide between the pair of cysteines at amino acid positions 272 and 281, wherein said amino acid positions are relative to the HCV polyprotein which is starting with the methionine of the Core protein at amino acid position 1 of said HCV polyprotein;

or selectively binding to a viral-like particle comprising any of said HCV E1 envelope proteins or parts thereof, antibodies capable of competing with said antibodies for selectively binding said HCV E1 envelope protein, or a fragment of any of said antibodies.

Said antibodies can be isolated from a mammal immunized with any of the above HCV E1 envelope proteins or parts thereof or with the above viral-like particle. Fragments of said antibodies can than be prepared. In particular said antibody or fragment thereof is a monoclonal antibody or a fragment thereof A specific antibody is the antibody secreted by the hybridoma cell line of DSM deposit with accession number ACC 2470. Again, fragments of this specific antibody can than be prepared. Determining if two antibodies are competing with each other for binding an epitope can easily be performed. Such experiments usually involve labeling of one of the two of said antibodies. Competition between antibodies can for instance be determined by comparing the amount of labeled antibody bound to the epitope of interest in the presence and absence, respectively, of the non-labeled antibody.

The present invention thus relates to an antibody to the HCV E1 envelope protein or part thereof according to the invention, and/or to a viral-like particle comprising said HCV E1 envelope protein. In particular, said antibody is raised upon immunization of a mammal with at least one protein as defined herein, or with a VLP comprising said protein. In a specific embodiment, said antibody is specifically reactive with a protein of the present invention, or with a viral-like particle comprising said protein. In particular the binding of said antibody to an HCV E1 envelope protein is dependent on the presence of at least one of the intramolecular disulfides present in the HCV E1 envelope protein as determined in the current invention. The selective binding of such antibodies to an HCV E1 envelope protein with at least one intramolecular disulfide as determined in the current invention is thus higher than the binding to an HCV E1 envelope protein without at least one of the intramolecular disulfides as determined in the current invention. Such antibodies are not hypothetical as the antibody IGH388 as disclosed in Example 7 hereafter binds with much higher affinity to an HCV E1 envelope protein with the intramolecular disulfides as determined in the current invention than to an HCV E1 envelope protein without disulfides. In a further specific embodiment, any of above-said antibodies is a monoclonal antibody or a humanized (monoclonal) antibody or a single-chain antibody. Fragments of any of above-said antibodies, e.g., $F_{ab}$, are also included in the term "antibody". In particular, said fragments retain the binding specificity of the complete antibody. The immunization process normally requires administration of said protein or part thereof, or of said viral-like particle comprising said protein, to said mammal.

The monoclonal antibodies of the invention can be produced by any hybridoma liable to be formed according to classical methods from splenic cells of an animal, particularly from a mouse or rat, immunized with an HCV protein according to the invention, or with a viral-like particles comprising said protein, on the one hand, and of cells of a myeloma cell line on the other hand. Hybridomas are subsequently selected which produce the monoclonal antibodies recognizing the protein or viral-like particle comprising said protein which has been initially used for the immunization of the animals. The invention also relates to the hybridoma cell line of DSM deposit with accession number ACC 2470 as outlined in Example 7.

The antibodies involved in the invention can be labeled by an appropriate label of the enzymatic, calorimetric, chemiluminescent, fluorescent, or radioactive type.

Non-human mammalian antibodies or animal antibodies can be humanized (see for instance Winter and Harris 1993). The antibodies or monoclonal antibodies according to the invention may be humanized versions of for instance rodent antibodies or rodent monoclonal antibodies. Humanisation of antibodies entails recombinant DNA technology, and is departing from parts of rodent and/or human genomic DNA sequences coding for H and L chains or from cDNA clones coding for H and L chains.

Alternatively, the monoclonal antibodies according to the invention may be human monoclonal antibodies. These antibodies according to the present embodiment of the invention can also be derived from human peripheral blood lymphocytes of patients immunized with a protein of the invention or with a VLP comprising said protein. Such human monoclonal antibodies are prepared, for instance, by means of human peripheral blood lymphocytes (PBL) repopulation of severe combined immune deficiency (SCID) mice (for recent review, see Duchosal et al. 1992) or by screening Epstein Barr-virus-transformed lymphocytes of immunized individuals for the presence of reactive B-cells by means of the antigens of the present invention.

The invention also relates to the use of the proteins or parts thereof or the use of VLPs comprising said proteins for the selection of recombinant antibodies by the process of repertoire cloning (Persson et al., 1991).

The invention further relates to the use of an antibody according to the invention for the manufacture of an immunogenic composition or a vaccine composition. In particular the immunogenic composition is an HCV immunogenic composition and the vaccine composition is an HCV vaccine composition, a therapeutic HCV vaccine composition or a prophylactic HCV vaccine composition. Any of these compositions can be used for immunizing a mammal against HCV infection or for treating a mammal infected with HCV.

Immunoassays and Diagnostic Kits

Methods for determining the presence of HCV antibodies in a sample are part of another embodiment of the invention, said methods comprising the steps of:

(i) contacting said sample with any of the above HCV E1 envelope proteins or parts thereof or with the above viral-like particle under conditions allowing the formation of an immunological antigen-antibody complex;

(ii) determining the immunological complex formed in (i);

(iii) inferring from (ii) the presence of HCV antibodies in said sample.

Methods for determining HCV E1 antigens in a sample are part of another embodiment of the invention, said methods comprising the steps of:

(i) contacting said sample with any of the above antibodies under conditions allowing the formation of an immunological antigen-antibody complex;

(ii) determining the immunological complex formed in (i);

(iii) inferring from (ii) the presence of HCV E1 antigens in said sample.

In particular, in step (i) of said methods any of the above HCV E1 envelope proteins or parts thereof, the above viral-like particle or any of the above antibodies is added as competitor; and said HCV E1 envelope protein or part thereof, viral-like particle or antibody used in said step (i), or said HCV E1 envelope protein or part thereof, viral-like particle or antibody added as competitor are labeled.

The invention additionally relates to diagnostic kits for determining the presence of HCV antibodies or HCV E1 envelope proteins in a sample, said kits comprising at least one of the above HCV E1 envelope proteins or parts, the above viral-like particle and/or any of the above antibodies.

The HCV E1 envelope proteins or parts thereof according to the present invention, or VLPs comprising said proteins, may be employed in virtually any inmmunoassay format that employs a known antigen to detect antibodies or a known antibody to detect antigens. A common feature of all of these assays is that the antigen is contacted with the body component containing or suspected of containing HCV antibodies or HCV antigens under conditions that permit binding between an antigen and an antibody, i.e. under conditions allowing the formation of an immunological complex. Such conditions will typically be physiologic temperature, pH and ionic strength using an excess of antigen (in the case of antibody detection) or antibody (in the case of antigen detection). The incubation of the antigen or antibody with the specimen is followed by detection of immune complexes.

The design of immunoassays is subject to a great deal of variation, and many formats are known in the art. Protocols may, for example, use solid supports, or immunoprecipitation. Most assays involve the use of labeled antibody and/or labeled polypeptide, e.g. a labeled peptide or polypeptide according to the present invention; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA and RIA assays. Other immunoassay designs comprise line immunoassays, sandwich immunoassays, antigen down immunoassays. An immunoassay may be set up in a competitive format.

An immunoassay may be, without limitation, in a heterogeneous or in a homogeneous format, and of a standard or competitive type. In a heterogeneous format, the protein is typically bound to a solid matrix, solid support or solid phase to facilitate separation of the sample from the protein after incubation. Examples of solid supports, matrices or phases are listed above. The solid support containing the antigenic proteins is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes that are formed. Both standard and competitive formats for these assays are known in the art.

In a standard format, the amount of antibodies, such as anti-HCV antibodies, in the antibody-antigen complexes is directly monitored. This may be accomplished by determining whether labeled anti-xenogeneic (e.g. anti-human) antibodies which recognize an epitope on said antibodies, such as said anti-HCV antibodies, will bind due to complex formation. In a competitive format, the amount of said antibodies, such as said anti-HCV antibodies, in a sample is deduced by monitoring the competitive effect on the binding of a known amount of (labeled) antibody (or other competing ligand) or antigen in the complex.

Antigen-antibody complexes can be detected by any of a number of known techniques, depending on the format. For example, unlabeled antibodies such as anti-HCV antibodies in the complex may be detected using a conjugate of anti-xenogeneic Ig complexed with a label (e.g. an enzyme label).

In an immunoprecipitation or agglutination assay format the reaction between an antigen and an antibody forms a protein cluster that precipitates from the solution or suspension and forms a visible layer or film of precipitate. If no antibody is present in the test specimen or sample, no such precipitate is formed.

A diagnostic kit usually comprises a molecule for detecting the presence of a sample reactant capable of interacting with said molecule, of a sample reactant modifying said molecule (e.g., in a chemical reaction), and/or of a sample reactant modifiable by said molecule (e.g., in a chemical reaction). In a diagnostic kit for detection of an antigen or antibody in a sample, one or more antibodies or antigens, respectively, are part of said kit. In a diagnostic kit for detecting antigens or antibodies, antibodies or antigens, respectively, are often present on a solid phase, matrix or support.

The proteins or parts thereof according to the present invention, or the VLPs comprising said proteins, can be packaged and be part of a diagnostic kit. The kit will normally contain in separate containers or vials the peptides or polypeptides according to the present invention (labelled or unlabelled), control antibody formulations (positive and/or negative), labelled antibody when the assay format requires the same and signal generating reagents (e.g. enzyme substrate) if the label does not generate a signal directly. The proteins according to the present invention may be already bound to a solid matrix or may be present in the kit in a separate vial together with reagents for binding it to the matrix. Instructions (e.g. written, tape, CD-ROM, etc.) for carrying out the assay usually will be included in the kit.

The signal-generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

Diagnostic kits for detecting antibodies to an HCV virus or for typing of an HCV virus wherein said kits comprise at least one protein according to the invention, or VLP comprising said protein, are part of the invention. In said diagnostic kit said protein or said VLP can be bound to a solid support.

Solid phases, solid matrices or solid supports on which the proteins or VLPs of the present invention, may be bound (or captured, absorbed, adsorbed, linked, coated, immobilized; covalently or non-covalently) comprise beads or the wells or cups of microtiter plates, or may be in other forms, such as solid or hollow rods or pipettes, particles, e.g., from 0.1 μm to 5 mm in diameter (e.g. "latex" particles, protein particles, or any other synthetic or natural particulate material), microspheres or beads (e.g. protein A beads, magnetic beads). A solid phase may be of a plastic or polymeric material such as nitrocellulose, polyvinyl chloride, polystyrene, polyamide, polyvinylidine fluoride or other synthetic polymers. Other solid phases include membranes, sheets, strips, films and coatings of any porous, fibrous or bibulous material such as nylon, polyvinyl chloride or another synthetic polymer, a natural polymer (or a derivative thereof) such as cellulose (or a derivative thereof such as cellulose acetate or nitrocellulose). Fibers or slides of glass, fused silica or quartz are other examples of solid supports. Paper, e.g., diazotized paper may also be applied as solid phase. Clearly, proteins of the present invention may be bound, captured, absorbed, adsorbed, linked or coated to any solid phase suitable for use in immunoassays. Said proteins can be present on a solid phase in defined zones such as spots or lines.

Any of the solid phases described above can be developed, e.g. automatically developed in an assay device.

With "developed" or "development" is meant that a sample or samples, suspected of comprising a binding partner to a molecule present on a solid phase, is or are applied to said solid phase and that the necessary steps are performed in order to detect binding of the binding partner to a molecule on a solid phase. This can, e.g., be the detection of binding of an antibody suspected to be present in a biological sample to or with an antigen, in casu a protein or peptide of the present invention, present on a solid phase. Automatic development hence refers to a development process, or any one or more steps thereof, in an automated or robotized fashion. A development automate or robot (or, generally, an assay device) generally is connected to or comprises one, more or all of the development or assay reagents and may in addition comprise a means to "read" the developed assay. Said "reading" will logically depend on the assay and may, e.g., confer to determining color intensities, to determining optical density or absorption at a given wavelength, to determining fluoresence, fosforescence or (chemi)luminescence, to determining turbidity, to determining the decay of a radio-active element or to determining other physical or physico-chemical characteristics that are related to the binding of a binding partner in a sample to a molecule present on a solid phase.

Another aspect of the invention relates to methods for screening compounds capable of modulating the binding between an HCV E1 envelope protein and an E1 ligand, said methods comprising:
(i) contacting said E1 ligand with any of the above HCV E1 envelope proteins or parts thereof with the above viral-like particle under conditions allowing the formation of an HCV E1-E1 ligand complex;
(ii) adding a compound suspected of modulating the binding between an HCV E1 envelope protein and an E1 ligand to the HCV E1-E1 ligand complex formed in (i);
(iii) determining the change in amount of HCV E1-E1 ligand complex formed in (i) and (ii);
(iv) inferring from (iii) whether the compound added in (ii) is a modulator of binding between an HCV E1 envelope protein and an E1 ligand.

Further methods for screening compounds capable of modulating the binding between an HCV E1 envelope protein and an E1 ligand, comprise the steps of:
(i) contacting, under conditions allowing the formation of an HCV E1-E1 ligand complex, said E1 ligand with any of the above HCV E1 envelope proteins or parts thereof or with the above viral-like particle in the presence and absence, respectively, of a compound suspected of modulating the binding between an HCV E1 envelope protein and an E1 ligand;
(ii) determining the amount of HCV E1-E1 ligand complex formed in (i) in the presence and absence of said compound;
(iii) inferring from (ii) whether said compound is a modulator of binding between an HCV E1 envelope protein and an E1 ligand.

In particular, in step (i) of said methods any of above HCV E1 envelope proteins or parts thereof or the above viral-like particle is added as competitor; and
said HCV E1 envelope protein or part thereof or viral-like particle used in said step (i), or
said HCV E1 envelope protein or part thereof or viral-like particle added as competitor are labeled.

E1 Ligands

Ligands of the HCV E1 envelope protein (i.e., E1 ligands) include peptides, antibodies or other molecules binding with E1, such as E1 ligands inhibiting the viral fusion or receptor domains, which are expected to be located on the HCV E1 envelope proteins. E1 ligands/(putative) HCV receptors known to date include L-SIGN and DC-SIGNR (Pohlmann et al. 2003), and apolipoprotein B, annexin V and tubulin (WO 99/24054) and heparin or derivatives thereof. A particular E1 ligand is an antibody of the current invention, such as an antibody specifically binding part of an E1 structure comprising an intramolecular disulfide of the invention, e.g. the monoclonal antibody IGH388 described herein.

Compounds

A compound capable of modulating the binding between an HCV E1 envelope protein and an E1 ligand can be a compound of any kind or chemical nature. Said compound can be of proteinaceous or non-proteinaceous nature. In particular said compound is targeting part of an E1 structure comprising an intramolecular disulfide bridge according to the invention. "Modulating" in this respect includes modification of the binding between an HCV E1 envelope protein and an E1 ligand in either way. Modulating thus includes increasing or decreasing the strenght of the binding between an HCV E1 envelope protein and an E1 ligand.

Another aspect of the invention envisages methods of producing a recombinant HCV E1 envelope protein or part thereof according to the invention, said methods comprising the steps of
(i) expressing of an HCV E1 envelope protein or part thereof in a eukaryotic host;
(ii) isolating from the pool of HCV E1 envelope protein or part thereof expressed in (i) the non-aggregated monomeric fraction of HCV E1 envelope protein or part thereof according to the invention.

Methods of producing a synthetic HCV E1 envelope protein or part thereof according to the invention are part of a further aspect wherein said methods comprise:
(i) chemical synthesis of an HCV E1 envelope protein or part thereof,
(ii) introducing during or after the chemical synthesis of an HCV E1 envelope protein or part thereof at least one disulfide as determined in the current invention.

Yet another aspect of the invention relates to the use of any of the above HCV E1 envelope proteins or parts thereof, the above viral-like particle and/or any of the above antibodies for the preparation of a medicament or a vaccine or for the preparation of an immunoassay or a diagnostic kit.

The use of any of the above HCV E1 envelope proteins or parts thereof or the above viral-like particle as a carrier of another protein or of a non-proteinaceous molecule form a further aspect of the invention.

Fusion Proteins and the HCV E1 Envelope Protein as Carrier Protein

The HCV E1 envelope protein or part thereof according to the present invention can further be flanked by at least one amino acid or amino acid sequence that is a non-HCV amino acid or amino acid sequence, or that is a HCV amino acid or amino acid sequence that is not naturally contiguous to said HCV E1 envelope protein (or part or variant thereof). Said flanking amino acid or amino acid sequence is contiguous with the the N- and/or C-terminus of the HCV E1 envelope protein (or part or variant thereof). Any fusion protein comprising an said HCV E1 envelope protein or part thereof is included in the present invention.

In particular the non HCV E1-part of any of such fusion proteins can be another HCV antigen (non-contiguous core, non-contiguous E1, E2, p7, NS2, NS3, NS4, NS5, or a part of any thereof; or a combination of any thereof) or an antigen of another pathogen such as, but not limited to, HBV (e.g., HBsAg or part thereof), HIV (e.g., p53 or part thereof), HTLV, influenza virus, pathogenic *Clostridia* species, pathogenic *Salmonella* species, pathogenic *Neisseria* species etc. Obviously the non HCV E1-part of any of such fusion proteins can be any other protein involved in provoking any disease symptom. In general the non HCV E1-part(s) of any of such fusion proteins comprises or consists of any epitope (B-cell epitope, T helper cell epitope, cytotoxic T cell epitope) of any given protein, or a combination of such epitopes (e.g., a polyepitope).

In the use of an HCV E1 envelope protein or part thereof, or a viral-like particle of any thereof, according to the present invention as a carrier of other proteins or of non-proteinaceous molecules said other proteins or non-proteinaceous molecules are linked to, or coupled to, or carried by said E1 or E1-part or E1-particle in a covalent or non-covalent fashion. In particular, any amino acid of said HCV E1 envelope protein or part thereof can be mutated to a lysine in order to facilitate directed (covalent) coupling of any other protein or of a non-proteinaceous molecule wherein said coupling is via the $\epsilon$-NH$_2$ group of the lysine. Even more particular, an arginine residue in the HCV E1 envelope protein or part thereof is mutated to a lysine. The carried other protein can be another HCV antigen (E1, E2, p7, NS2, NS3, NS4, NS5, or a part of any thereof, or a combination of any thereof) or an antigen of another pathogen such as, but not limited to, HBV (e.g., HBsAg or part thereof), HIV (e.g., p53 or part thereof), HTLV, influenza virus, pathogenic *Clostridia* species, pathogenic *Salmonella* species, pathogenic *Neisseria* species etc. In general the carried protein comprises or consists of any epitope (B-cell epitope, T helper cell epitope, cytotoxic T cell epitope) of any given protein, or a combination of such epitopes (e.g., a polyepitope). Obviously the carried other protein can be any other protein involved in provoking any disease symptom. Carried non-proteinaceous molecules include any molecule with prophylactic or therapeutic action.

Thus the invention covers isolated proteins comprising an HCV E1 envelope protein or part thereof according to the invention. In particular said isolated protein is further comprising at least one of:

an N-terminal flanking amino acid or amino acid sequence of an HCV protein or part thereof not naturally contiguous with said HCV E1 envelope protein or part thereof, a C-terminal flanking amino acid or amino acid sequence of an HCV protein or part thereof not naturally contiguous with said HCV E1 envelope protein or part thereof, an N-terminal flanking non-HCV amino acid or amino acid sequence;

a C-terminal flanking non-HCV amino acid or amino acid sequence.

Alternatively, said isolated protein is comprising the HCV E1 envelope protein or part thereof as carrier protein.

The invention further relates to methods for inducing immunity or an immune response in healthy or HCV-infected mammals wherein said methods comprise administering the HCV E1 envelope protein or part thereof according to the invention, or the viral-like particle comprising it, to said mammals. The invention further relates to methods for passively immunizing healthy or HCV-infected mammals wherein said methods comprise administering an antibody to an HCV E1 envelope protein or part thereof according to the invention to said mammals. In particular said mammal is a human.

EXAMPLES

Example 1

Purification of Monomeric HCV E1 Envelope Protein Population

The HCV E1s protein (amino acids 192-326: YEVRNVS-GMYHVTNDCSNSSIVYEAADMIMHTPGCVPCV RENNSSRCWVALTPTLA ARNASVPTTTIRRHVDLLV-GAAAFCSAMYVGDLCGSVFLVSQLFT-ISPRRHETVQDC NCSIYPGHITGHRMAWDMMMNW; SEQ ID NO:1) was expressed in *Hansenula polymorpha* cells as described in, e.g., Example 16 of International Patent Publication WO 02/086101. The HCV E1s protein was purified without disruption of intra- and intermolecular disulfide bridges as outlined below.

Since the HCV E1s (aa 192-326) was expressed as a C-terminal (His)6-tagged protein [(CL)-E1s-(His)$_6$], a first capture and purification step of the Gu.HCl-solubilized product could be performed on Ni-IDA after cell disruption and clarification.

In brief, cell pellets were resuspended in 6 M Gu.HCl, 10 mM iodoacetamide, 100 mM HEPES, pH 8.0[ 2 mL buffer/g cells (wet weight)]. Iodoacetamide was added to block present free thiol groups. After homogenisation of the cell suspension, cells were disrupted by high-pressure homogenisation (3 passages at 1.8 kbar and 10° C. on a high-pressure homogenizer, Constant Systems). The lysate was clarified by centrifugation (13.000×g for 1 hour at 4° C.). The obtained supernatant was diluted 4 times with 6 M Gu.HCl, 50 mM phosphate, pH 7.2 and n-dodecyl-N,N-dimethylglycine (also known as lauryldimethylbetaine or Empigen BB®, Albright & Wilson) and imidazole were added to a final concentration of 1% (w/v) and 20 mM respectively.

All further chromatographic steps were executed on an Akta FPLC (or Explorer) workstation (Pharmacia). The sample was filtrated through a 0.22 µm pore size membrane (cellulose acetate) and loaded on a Ni$^{2+}$-IDA column (Chelating Sepharose FF, Pharmacia), that was equilibrated with 50 mM phosphate, 6 M Gu.HCl, 1% Empigen BB, pH 7.2 (IMAC-A buffer) supplemented with 20 mM imidazole. The column was washed sequentially with IMAC-A buffer containing 20 mM and 50 mM imidazole respectively till the absorbance at 280 nm reached the baseline level. A further washing and elution step of the his-tagged products was performed by the sequential application of IMAC-B buffer (PBS, 1% Empigen BB, pH 7.2) supplemented with 50 mM irnidazole and 200 mM imidazole, respectively. The fractions were analysed by SDS-PAGE (and silver staining) and western-blot using a specific monoclonal antibody directed against E1s (IGH201). The elution fractions containing mainly E1s were pooled ('IMAC pool') and concentrated 20 times by ultrafiltration (MWCO 10 kDa, centriplus, Amicon, Millipore).

In order to separate the monomeric E1s from the oligomeric fraction, the concentrated sample was loaded on a Superdex® 200 HR 10/30 column (Pharmacia) equilibrated with PBS, 3% (w/v) n-dodecyl-N,N-dimethylglycine. Fractions were screened for the presence of monomeric E1s by SDS-PAGE under reducing and non-reducing conditions (and silver staining) and western-blot analysis using a specific monoclonal antibody directed against E1s (IGH201). This analysis showed that fractions containing monomeric E1s (Mr between ~10 kDa and ~35 kDa based on the migration on non-reducing SDS-PAGE) with a purity of more than 90% could be separated. These fractions were pooled ('SEC pool') for further virus like particle (VLP) formation. Western blotting and peak integration of the IMAC- and SEC-runs indicated that the monomeric E1s fraction constitutes less than 5% of the total intracellular E1s protein population. Removal of the E1s in intermolecularly disulfide-linked material was thus necessary for obtaining a monomeric E1s population allowing the accurate analysis and localization of intramolecular disulfide bridges. After PNAGase F-treatment of the monomeric E1s fraction, all proteins migrate between Mr 10 kDa and ~25 kDa in a non-reducing SDS-PAGE gel.

VLP formation of the purified monomeric E1s was enforced by exchanging n-dodecyl-N,N-dimethylglycine for 3% betain. For (His)$_6$-tagged E1s, this buffer switch was realized on a Ni$^{2+}$-IDA column. Therefore, the 'SEC pool' was 3 times. diluted in PBS buffer to a final concentration of PBS, 1% (w/v) n-dodecyl-N,N-dimethylglycine, pH 7.5 and was applied to a Ni$^{2+}$-IDA column (Chelating Sepharose FF, Pharmacia), that was equilibrated with PBS, 1% (w/v) n-dodecyl-N,N-dimethylglycine, pH 7.5. Further VLP formation was accomplished by application of 7 column volumes washing buffer (PBS, 3% (w/v) betaine, pH 7.5). Elution of the obtained VLPs was accomplished by addition of 500 mM imidazole to this buffer. After pooling of the elution fractions, Dynamic Light Scattering Analysis (using a particle-size analyser Model Zetasizer 1000 HS, Malvern Instruments Ltd, controlled by photon correlation spectroscopy (PCS) software) on the final product showed the presence of E1s-particles with an average size of 29 nm. Furthermore, SDS-PAGE (and silver staining) and western-blot analysis using a specific monoclonal antibody directed against E1s (IGH201) indicated that the final VLP product—obtained by an initial purification of monomeric E1s without disruption of disulfide bridges—is obtained with more than 90% purity (see FIG. 2A for silver-stained gel, and FIG. 2B for western blot).

The hybridoma cell line producing the monoclonal antibody directed against E1 (IGH201) was deposited on Mar. 12, 1998 under the conditions of the Budapest Treaty at the European Collection of Cell Cultures, Centre for Applied Microbiology & Research, Salisbury, Wiltshire SP4 OJG, UK, and has the accession number ECACC 98031216.

Example 2

Localization of Disulfide Bridges in Monomeric E1s Population Using Tryptic Digestion In order to find disulfide bridges in the monomeric E1s fraction purified as in Example 1, this product was compared to a fully reduced and sulphonated E1s-(His)6 prepared as described in, e.g., Example 15 of International Patent Publication WO 02/086101, further referred to as sulphonated E1s.

This sulphonated E1s sample was used as control sample and treated in the same way as the monomeric E1s material from Example 1.

In order to generate a tryptic digest the following steps were applied to both samples:

Alkylation with iodoacetamide, to block cysteines that are free: the material was incubated in 20 mM iodoacetamide during 20 minutes, in the dark at room temperature.

Deglycosylation with PNGase F: PNGase F was added to reach a concentration of 0.2 U/µg E1s. The PNGase F digest was incubated overnight at 37° C., in the dark (because of the presence of iodoacetamide).

Purification of deglycosylated E1s on RPC: purification was performed using a Vydac C4, 2.1 mm×250 mm column. The following gradient was used 0 min–20% B, 5 min–20 % B, 65 min–80% B, 66 min–20% B, 86 min–20% B (solvent A: 0.1% TFA in water, solvent B: 0.1% trifluoroacetic acid (TFA) in acetonitrile, flow: 150 µL/min).

Trypsine digestion in solution was performed at a 1/20 enzyme/substrate ration (buffer 50 mM NH$_4$HCO$_3$ pH 7.8, 1 M urea, 10% acetonitrile; incubation: overnight at 37° C.).

Purification of 5 µg of tryptic peptides was performed by ZipTip C18 (elution in 3 µl 80% acetonitrile/0.1% TFA), followed by mass spectrometry (MALDI-TOF-MS) in linear and reflector mode (dried droplet method).

A theoretical exercise based on the E1s protein sequence learns that the peptides as presented in Table 1 can theoretically be generated by a tryptic digest.

Analysis of the MALDI-TOF-MS spectrum of the tryptic digest, allowed to assign a number of peaks to theoretical peptides as presented in Table 1. An overview of the assigned MALDI-TOF-MS peaks is given in Table 2. Peptides recovered only from the monomeric E1s protein but not from the control sulphonated E1s are highlighted.

From Table 2 the following conclusions are formulated:

Surprisingly only trace amounts of the peptides expected on the basis of Garry and Dash (2003) were recovered;

One disulfide bridge was present in the T2 peptide;

A disulfide bridge was linking T2 to T4;

Some masses could be assigned to T2/T4, containing two S-S-bridges;

One disulfide bridge was present in the T7 peptide, and the cysteines of T7 were apparently not involved in bridging T7 with other peptides. The cysteine bridge within T7 was formed with high efficiency as MS-spectra do not support the presence of alkylated T7 forms;

The two cysteines, which are in the T9-peptide, were only measured in the alkylated form, so the T9 peptide does not contain a disulfide bridge and the cysteines are apparently also not involved in bridging T9 with other peptides;

Some peaks of the sulphonated E1s were assigned to peptides having a disulfide bridge within T2 or linking T2/T4, these peptides could have been present in the starting material or may have formed during the treatment of the samples as sulphonation can be reversed;

General remarks:
  (i) the material was overalkylated, probably because PNGase F digestion has been performed in the presence of iodoacetamide. This explains the modification of methionine to dehydroamino-2-butyric acid (Dhb) and to alkylated methionine (+42.99 Da) (Lapko et al. 2000). The overalkylation of the His$_6$ tail is probably the reason why T10 was not measured.

(ii) The indications "W→D" in Tables 1 and 2 (as well as in Table 3) refer to the phenomenon in which a tryptophan (186.21 Da) degrades to a mass of 115.1 Da, i.e. putatively asparagine. This phenomenon has also been observed in other proteins analysed by mass spectrometry after liquid chromatography, e.g., for tryptophan at position 61 in the human transthyretin.

TABLE 1

Theoretical tryptic digest of E1s-(His)6. Where appropriate, peptides expected based on Gary and Dash (2003) have also been indicated. The numbering of the amino acids presented for E1 starts at 1 and can be compared with the HCV polyprotein in which the first amino acid of E1 is 192, by adding 191. A schematic representation of the cysteines in the E1 and E1s protein is depicted in FIG. 1.

| Fragment # | Amino acid start-end | Sequence | SEQ ID NO |
|---|---|---|---|
| Reduced S—S-bridges (free cysteines-SH HS—) | | | |
| T1 | 1-4 | YEVR | 2 |
| T2 | 5-40 | DVSGMYHVTNDCSDSSIVYEAADMIMHTPGCVPCVR | 3 |
| T3 | 41-46 | ENDSSR | 4 |
| T4 | 47-58 | CWVALTPTLAAR | 5 |
| T5 | 59-68 | DASVPTTTIR | 6 |
| T6 | 69-69 | R | |
| T7 | 70-105 | HVDLLVGAAAFCSAMYVGDLCGSVFLVSQLFTISPR | 7 |
| T8 | 106-106 | R | |
| T9 | 107-126 | HETVQDCDCSIYPGHITGHR | 8 |
| T10 | 127-141 | MAWDMMMNWHHHHHH | 9 |

| Theoretical S—S-bridges potentially present in following peptides or peptide combinations | | | | Expected by Garry and Dash 2003 |
|---|---|---|---|---|
| T2 | 5-40 | DVSGMYHVTNDCSDSSIVYEAADMIMHTPGCVPCVR | 3 | |
| T7 | 70-105 | HVDLLVGAAAFCSAMYVGDLCGSVFLVSQLFTISPR | 7 | |
| T9 | 107-126 | HETVQDCDCSIYPGHITGHR | 8 | |
| T2/T4 | 5-40 | DVSGMYHVTNDCSDSSIVYEAADMIMHTPGCVPCVR | 3 | |
| | 47-58 | CWVALTPTLAAR | 5 | |
| T2/T7 | 5-40 | DVSGMYHVTNDCSDSSIVYEAADMIMHTPGCVPCVR | 3 | linked by one bridge |
| | 70-105 | HVDLLVGAAAFCSAMYVGDLCGSVFLVSQLFTISPR | 7 | |
| T2/T9 | 5-40 | DVSGMYHVTNDCSDSSIVYEAADMIMHTPGCVPCVR | 3 | linked by two bridges |
| | 107-126 | HETVQDCDCSIYPGHITGHR | 8 | |
| T4/T7 | 47-58 | CWVALTPTLAAR | 5 | linked by one bridge |
| | 70-105 | HVDLLVGAAAFCSAMYVGDLCGSVFLVSQLFTISPR | 7 | |
| T4/T9 | 47-58 | CWVALTPTLAAR | 5 | |
| | 107-126 | HETVQDCDCSIYPGHITGHR | 8 | |
| Combinations of three or more peptides may also be possible | | | | |

TABLE 2

Assigned MALDI-TOF-MS peaks for tryptic digests of monomeric and sulphonated E1s. The numbering of the amino acids presented for E1 starts at 1 and can be compared with the HCV polyprotein in which the first amino acid of E1 is 192, by adding 191. Sulphonated cysteines are generally measured as free cysteines (desulphonation during MALDI-TOF-MS).

| Corresponding Table 1 number | Amino Acid start-end | Interpretation | Theoretical mass (monoisotopic) | Theoretical mass (average) | Measured mass (M + H)+ Sulphonated E1s | Measured mass (M + H)+ Monomeric E1s |
|---|---|---|---|---|---|---|
| T5 | 59-68 | | 1058.57 | | 1059.70 | 1059.64 |
| T4 | 47-58 | free C | 1300.70 | | 1301.86 | 1301.80 |
| T4 | 47-58 | free C + 2*O | 1332.68 | | 1333.90 | — |
| T4 | 47-58 | C = cys-CAM/—NH$_3$ | 1340.70 | | 1341.89 | 1341.82 |
| T4 | 47-58 | C = cys-CAM | 1357.72 | | 1358.89 | 1358.84 |
| T4 | 47-58 | C = cys-CAM/—NH$_3$/+2*O | 1372.68 | | 1373.89 | 1373.81 |
| T4 | 47-58 | C = cys-CAM/+2*O | 1389.70 | | 1390.89 | 1390.81 |
| T4 | 47-58 | Free C + 162.05 Da | 1462.75 | | 1463.95 | — |
| T4 | 47-58 | C = cys-CAM/—NH$_3$/+162.05 Da | 1502.75 | | 1503.97 | 1503.87 |
| T4 | 47-58 | C = cys-CAM/+162.05 Da | 1519.77 | | 1521.01 | 1520.92 |
| T9 | 107-126 | 1 C = cys-CAM/1 free C | 2323.01 | | 2324.26 | — |
| T9 | 107-126 | 2 C = cys-CAM | 2380.03 | | 2381.24 | 2381.23 |
| T9 | 107-126 | 2 C = cys-CAM/+57.02 Da | 2437.05 | | 2438.33 | 2438.18 |
| T8-9 | 106-126 | 2 C = cys-CAM | 2536.13 | | 2537.43 | 2537.35 |
| T8-9 | 106-126 | 2 C = cys-CAM/+57.02 Da | 2593.15 | | 2594.46 | 2594.36 |
| T7 | 70-105 | S—S-bridge/1 M = Dhb | | 3738.34 | — | 3738.91 |
| T7 | 70-105 | 2 free C/1 M = Dhb | | 3740.36 | 3742.06 | — |

TABLE 2-continued

Assigned MALDI-TOF-MS peaks for tryptic digests of monomeric and sulphonated E1s. The numbering of the amino acids presented for E1 starts at 1 and can be compared with the HCV polyprotein in which the first amino acid of E1 is 192, by adding 191. Sulphonated cysteines are generally measured as free cysteines (desulphonation during MALDI-TOF-MS).

| Corresponding Table 1 number | Amino Acid start-end | Interpretation | Theoretical mass (monoisotopic) | Theoretical mass (average) | Measured mass $(M + H)^+$ Sulphonated E1s | Measured mass $(M + H)^+$ Monomeric E1s |
|---|---|---|---|---|---|---|
| T7 | 70-105 | S—S-bridge/1 M = Dhb/+57.02 Da | | 3795.36 | — | 3797.02 |
| T7 | 70-105 | 1 free C/1 C = cys-CAM/1 M = Dhb | | 3797.37 | 3799.37 | — |
| T7 | 70-105 | S—S-bridge/+57.02 Da | | 3843.47 | — | 3844.05 |
| T7 | 70-105 | 1 free C/1 C = cys-CAM | | 3845.49 | 3846.97 | — |
| T2 | 5-40 | S—S-bridge/free C/1 M = Dhb | | 3854.35 | 3856.02 | 3854.88 |
| T2 | 5-40 | S—S-bridge/free C | | 3902.46 | 3903.27 | 3902.48 |
| T2 | 5-40 | S—S-bridge/1*C = cys-CAM/1 M = Dhb | | 3911.37 | — | 3911.45 |
| T2 | 5-40 | S—S-bridge/1 C = cys-CAM | | 3959.48 | 3960.46 | 3959.85 |
| T2 | 5-40 | S—S-bridge/1 C = cys-CAM/1 M = Dhb/+57.02 Da/+42.99 Da (IAM on M) | | 4011.38 | — | 4011.60 |
| T2 | 5-40 | S—S-bridge/1 C = cys-CAM/+57.02 Da/+42.99 Da (IAM on M) | | 4059.49 | — | 4059.32 |
| T2 | 5-40 | S—S-bridge/1 C = cys-CAM/+2*57.02 Da/+42.99 Da (IAM on M) | | 4116.51 | — | 4115.97 |
| T2/T4 | 5-40/47-58 | 2 S—S-bridges/W → D/2 M = Dhb/1*O | | 5050.65 | — | 5052.95 |
| T2/T4 | 5-40/47-58 | 1 S—S-bridge/2 free C/W → D/2 M = Dhb/1*O | | 5052.66 | ? 5054.37 | — |
| T2/T4 | 5-40/47-58 | 2 S—S-bridges/W → D/1 M = Dhb/1*O | | 5098.75 | ? 5100.59 | 5100.28 |
| T2/T4 | 5-40/47-58 | 2 S—S-bridges/W → D/1 M = Dhb/1*O/+42.99 Da (IAM on M) | | 5141.74 | — | 5142.71 |
| T2/T4 | 5-40/47-58 | 2 S—S-bridges/W → D/1 M = Dhb/1*O/+57.02 Da | | 5155.77 | — | 5157.76 |
| T2/T4 | 5-40/47-58 | 2 S—S-bridges/W → D/1 M = Dhb/1*O/+42.99 Da (IAM on M)/+2*57.02 Da | | 5255.78 | — | 5256.84 |

Cys-CAM = acetamide-derivative of cysteine;
IAM on M = acetamide-derivative of methionin;
W → D = artefactual degradation of tryptophan to aspartate (see General remark (ii) in Example 2).

Example 3

Further Support for Localization of Disulfide Bridges in the Monomeric E1s by Tryptic Digestion, Using Additional Reduction and Alkylation Five microgram of the tryptic digest sample of the monomeric E1s from Example 2 was reduced with DTT followed by alkylation with iodoacetamide. The material was purified by ZipTip C18, eluted in 3 μL of 80% acetonitrile/0.1% TFA and analyzed by MALDI-TOF-MS.

The MALDI-TOF-MS measurement of the tryptic digest of the monomeric sample, before and after reduction/alkylation, was compared and is summarized in Table 3.

From Table 3 the following conclusions are formulated:
  The peaks coming from T7 with an S-S-bridge (3738.96, 3979.31 and 3844.17 Da), disappeared after reduction and alkylation with iodoacetamide. One peak at mass 3846.80 Da can be explained as T7 with a reduced S-S-bridge (1 C=cys-CAM). This provides further evidence for the existence of a disulfide bridge in T7;
  The masses between 3854.91 Da and 4115.29 Da all increased with 2 Da after reduction but it seems that alkylation of the thiols did not take place. This is indicative for an S-S-bridge in the T2-peptide, which was reduced after reduction and alkylation;
  The masses around 5100.29 Da disappeared after reduction and alkylation, which provided evidence for the S-S-bridge between T2 and T4.

From the combined results of Examples 2 and 3 it is concluded that:
  the cysteines in T9 were not involved in a disulfide bridge;
  the cysteine in T7 were involved in a intra-peptide disulfide bridge, thus allowing the localization of a first disulfide bridge between amino acids 272 and 281;
  a second disulfide bridge was present between T2 and T4 thus linking amino acid 238 with either amino acid 207 or 226 or 229;
  a third disulfide bridge was present within the T2 peptide and thus links either amino acid 207 with 226 or 207 with 229 or 226 with 229.

TABLE 3

Assigned MALDI-TOF-MS peaks for tryptic digests of monomeric E1s with or without additional DTT/iodoacetamide treatment. The numbering of the amino acids presented for E1 starts at 1 and can be compared with the HCV polyprotein in which the first amino acid of E1 is 192, by adding 191.

| Corresponding | | | Theoretical | Measured mass $(M + H)^+$ for monomeric E1s | |
|---|---|---|---|---|---|
| Table 1 number | Amino acid start-end | Interpretation | mass (average) | | +DTT +Iodoacetamide |
| T7 | 70-105 | S—S-bridge/1 M = Dhb | 3738.34 | 3739.04 | — |
| T7 | 70-105 | S—S-bridge/1 M = Dhb/+57.02 Da | 3795.36 | 3797.26 | — |
| T7 | 70-105 | S—S-bridge/+57.02 Da | 3843.47 | 3844.94 | — |
| T7 | 70-105 | S—S bridge reduced/1 C = cys-CAM | 3845.48 | — | 3846.80 |
| T2 | 5-40 | S—S-bridge/free C/1 M = Dhb | 3854.35 | 3854.78 | — |
| T2 | 5-40 | S—S-bridge reduced/free C/1 M = Dhb | 3856.36 | — | 3858.76 |
| T2 | 5-40 | S—S-bridge/free C | 3902.46 | 3902.54 | — |
| T2 | 5-40 | S—S-bridge reduced/free C | 3904.47 | — | 3905.33 |
| T2 | 5-40 | S—S-bridge/1 C = cys-CAM/1 M = Dhb | 3911.37 | 3911.21 | — |
| T2 | 5-40 | S—S-bridge/1 C = cys-CAM | 3959.48 | 3959.44 | — |
| T2 | 5-40 | S—S-bridge reduced/1 C = cys-CAM | 3961.49 | — | 3962.45 |
| T2 | 5-40 | S—S-bridge/1 C = cys-CAM/1 M = Dhb/+57.02 Da/+42.99 Da (IAM on M) | 4011.38 | 4012.00 | — |
| T2 | 5-40 | S—S-bridge/1 C = cys-CAM/+57.02 Da/+42.99 Da (IAM on M) | 4059.49 | 4059.10 | — |
| T2 | 5-40 | S—S-bridge reduced/2 C = cys-CAM/1 free cys/+42.99 Da (IAM on M) | 4061.50 | — | 4062.15 |
| T2 | 5-40 | S—S-bridge reduced/3 C = cys-CAM | 4075.53 | — | 4076.30 |
| T2 | 5-40 | S—S-bridge/1 C = cys-CAM/+2*57.02 Da/+42.99 Da (IAM on M) | 4116.51 | 4115.95 | — |
| T2 | 5-40 | S—S-bridge reduced/3 C = cys-CAM/+42.99 Da (IAM on M) | 4118.52 | — | 4118.57 |
| T2/T4 | 5-40/47-58 | 2 S—S-bridges/W → D/2 M = Dhb/1*O | 5050.65 | 5052.95 | — |
| T2/T4 | 5-40/47-58 | 2 S—S-bridges/W → D/1 M = Dhb/1*O | 5098.75 | 5100.28 | — |
| T2/T4 | 5-40/47-58 | 2 S—S-bridges/W → D/1 M = Dhb/1*O/+42.99 Da (IAM on M) | 5141.74 | 5142.71 | — |
| T2/T4 | 5-40/47-58 | 2 S—S-bridges/W → D/1 M = Dhb/1*O/+57.02 Da | 5155.77 | 5157.76 | — |
| T2/T4 | 5-40/47-58 | 2 S—S-bridges/W → D/1 M = Dhb/1*O/+42.99 Da (IAM on M)/+2*57.02 Da | 5255.78 | 5256.84 | — |

Cys-CAM = acetamide-derivative of cysteins;
IAM on M = acetamide-derivative of methionine;
W → D = artefactual degradation of tryptophan to aspartate (see General remark (ii) in Example 2).

Example 4

Unraveling the Disulfide Bridges within T2 and Linking T2 with T4

In order to unravel the localization of the disulfide bridges within T2 end T2/T4, a number of peptides were analyzed. A first experiment was designed to find out whether the two first cysteines in the sequence of T2, i.e. cysteines 207 and 226 are forming a disulfide bridge. As additional controls, a peptide was analyzed containing the cysteines of T9 which apparently are unable to bridge and a peptide containing the cysteines of T7 which based on the evidence of examples 2 and 3 should be forming an intrapeptide bridge.

The peptides are:
IGP 1634: Ac-SQLFTISPRRHETVQDCNCS-NH$_2$ (SEQ ID NO:10); contains the cysteines of T9 and is further referred to as T9';
IGP 2133: Ac-AFCSAMYVGDLCGS-NH$_2$ (SEQ ID NO:11); contains the cysteines of T7 and is further referred to as T7'; and
IGP 2134: Ac-NDCSNSSIVYEAADMIMHTPGCVP-NH$_2$ (SEQ ID NO:12); contains the first 2 cysteines of T2 and is further referred to as T2' wherein Ac is acetyl.

These peptides were dissolved at 450 µM in 0.1% TFA except T7'. Due to its lower solubility T7' was dissolved at 300 µM in dichloromethane (DCM). Peptide stock solutions or mixtures thereof as shown below were dispensed in 4 mL glass vials (Wheaton) and dried using speed-vacuum drying. To study the interaction of each individual peptide, a complete set of different. peptide combinations was prepared:
homogeneous peptide solutions: T2', T7', and T9'
heterogeneous di-peptide mixtures: T2' and T7', T2' and T9', and T7' and T9'
heterogeneous tri-peptide mixtures: T2' and T7' and T9'

MALDI-TOF-MS analysis confirmed that the individual peptides were reduced, with free thiols, at the start of the experiment (see Table 4). Samples were obtained from the 10-fold acidic stock solutions prior to speed-vacuum drying.

TABLE 4

Low range MALDI-TOF-MS measurements (500-3000 Da) of 10-fold stock solutions.

| | Reduced peptide | | |
|---|---|---|---|
| Peptide stock | Theoretical mass (monoisotopic) | Measured mass M + H$^+$ (monoisotopic) | Interpretation |
| T7' (IGP 2133) | 1463.6 | 1486.5 (Na adduct) | free Cys |
| T2' (IGP 2134) | 2594.1 | 2595.0 | free Cys |
| T9' (IGP 1634) | 2361.1 | 2362.4 | free Cys |

Oxidation of the peptide or peptide mixtures was initialised by adding 1 mL of 0.1 M NH$_4$HCO$_3$ pH 8.0 and stirring in close contact with air. Estimated net peptide concentration of this final oxidation mixture was 45 µM or 65.8, 116.7 and 108.6 µg/mL for T7', T2' and T9' respectively. The oxidation was stopped after 31 hours by adding 1% TFA and 10% acetonitrile (pH~=2) and vials were stored at −20° C. Simultaneously, a 1 µL sample was spotted for MALDI-TOF-MS analysis and combined with 1 µL matrix mixture (dried droplet). After drying, the spot was re-dissolved in situ using 1 µL 1% TFA/70% acetonitrile. By "in situ" acidification, peptide precipitation was avoided. The details of the MALDI matrix and instrument setting can be found in Table 5, and the results in Tables 6 (low range: 500-3000 Da) and 7 (mid range: 3000-10000 Da).

TABLE 5

MALDI matrix and instrument settings used as a function of the targeted mass range

| Structure | Mass range (Da) | Matrix | Settings |
|---|---|---|---|
| monomer peptide | 500-3000 | 20 mg/ml α-cyano in 70% acetonitrile/0.1% TFA | Reflector mode (Monoisotopic mass) |
| di- and trimer peptide | 3000-10000 | 10 mg/ml sinapinic acid/10 mg/ml fucose in 50% acetonitrile/0.1% TFA | Linear mode (Average mass) |

TABLE 6

Low range MALDI-TOF-MS measurements (500-3000 Da) after 31 h oxidation.

| | Oxidised peptides | | |
|---|---|---|---|
| Peptide solution | Theoretical mass (monoisotopic) | Measured mass M + H$^+$ (1° isotope) | Interpretation |
| T7' | 1461.6 | 1484.6 (Na adduct) | intra-molecular S—S bridged |
| T2' | 2592.1 | 2593.4 | intra-molecular S—S bridged |
| T9' | 2359.1 | 2360.1 | intra-molecular S—S bridged |
| T7'/T2' | 1461.6/2592.1 | 1484.5 (Na$^+$)/2593.0 | intra-molecular S—S bridged |
| T2'/T9' | 2592.1/2359.1 | 2593.0/2359.9 | intra-molecular S—S bridged |
| T7'/T9' | 1461.6/2359.1 | 1484.4 (Na$^+$)/2359.8 | intra-molecular S—S bridged |
| T7'/T2'/T9' | 1461.6/2592.1/2359.1 | 1484.4 (Na$^+$)/2592.6/2359.6 | intra-molecular S—S bridged |

To illustrate the clear signals of T9'↔T9' dimers versus the signals that corresponds with traces of intermolecular disulfide bridging involving T7' and T2' (T7'↔T9', T7'↔T2', T2'↔T9', T2'↔T2', T7'↔T7') the mass spectrum of the T7'↔T2'↔T9' solution after 31 h of oxidation is shown in FIG. 3. The T9' peptide preparation contained a peptide synthesis side product consisting of the T9' sequence with one out of the two threonine residues lacking (T9' Thr del). This side product was also recovered in part in dimers, explaining the additional peak in FIG. 3.

Data obtained for the mid range showed that T9' multimers (mainly dimers) are formed independent from the presence of one or both of the other peptides. From this it is obvious that, even though inter-molecular interaction in this set-up is possible, as shown by the T9' dimerisation, intra-molecular disulfide bounds are favourable for T7' and T2'. This selectivity for intra-molecular interaction of T7' and T2', possibly induced through energetically favourable folding of the individual peptide, is indicative for the presence of these disulfide bounds in the E1s protein localized in T2' and T7' and not in T9'. None or only minor traces (FIG. 3) of intermolecular disulfide bridging involving T7' and T2' (T7'↔T9', T7'↔T2', T2'↔T9') were detected.

From these oxidation experiments it is concluded that:

The lack of a disulfide bridge in T9 between amino acids 304 and 306 as evident from Example 2 was further supported by the finding that intramolecular disulfide bridging which is almost exclusively found for T2' and T7, is for T9' accompanied with a significant amount of intermolecularly disulfide bridged peptides. Consequently the driving force to form an intramolecular bridge between T2' and T7' seems to be higher than for T9'. In the context of E1s this leads to the absence of detectable amounts of disulfide bridges between amino acids 304 and 306;

The disulfide bridge within T2 was localized between aa 207 and 226 as in T2';

Consequently the disulfide bridge between T2 and T4 should be localized between 229 and aa 238;

No evidence was found for other disulfide bridge interactions.

TABLE 7

Mid range MALDI-TOF-MS measurements (3000-10000 Da) after 31 h oxidation.

| | Oxidised peptides | | |
|---|---|---|---|
| Peptide solution | Theoretical mass dimer peptide (average) | Measured mass M + H$^+$ | Interpretation |
| T7' | 2925.4 (T7'↔T7' dimer) | — | |
| T2' | 5187.6 (T2'↔T2' dimer) | — | |
| T9' | 4721.2 (T9'↔T9' dimer) | 4723.54 | 2 × S—S inter-molecular linked T9'↔T9' dimer |
| | 4620.1 (T9'↔Thr deletion dimer) | 4622.41 | 2 × S—S inter-molecular linked T9'↔T9' (Thr del) dimer |
| | 7083.9 (T9'↔T9'↔T9' trimer) | 7083.7 | 3 × S—S inter-molecular linked T9'↔T9'↔T9' trimer |
| | 9446.5 | 9446.81 | |

TABLE 7-continued

Mid range MALDI-TOF-MS measurements (3000-10000 Da) after 31 h oxidation.

Oxidised peptides

| Peptide solution | Theoretical mass dimer peptide (average) | Measured mass M + H⁺ | Interpretation |
|---|---|---|---|
| | (T9'↔T9'↔T9'↔T9' tetramer) | | 4 × S—S inter-molecular linked T9'↔T9'↔T9'↔T9' tetramer |
| T7'/T2' | 2925.4 (T7'↔T7' dimer) | — | |
| | 5187.6 (T2'↔T2' dimer) | 5187.2 | 2 × S—S inter-molecular linked T2'↔T2' dimer (trace) |
| | 4056.6 (T7'↔T2' dimer) | — | |
| T2'/T9' | 5187.6 (T2'↔T2' dimer) | — | |
| | 4721.2 (T9'↔T9' dimer) | 4723.7 | 2 × S—S inter-molecular linked T9'↔T9' dimer |
| | 4954.5 (T2'↔T9' dimer) | — | |
| T7'/T9' | 2925.4 (T7'↔T7' dimer) | — | |
| | 4721.2 (T9'↔T9' dimer) | 4722.8 | 2 × S—S inter-molecular linked T9'↔T9' dimer |
| | 3823.3 (T7'↔T9' dimer) | — | |
| T7'/T2'/T9' | 2925.4 (T7'↔T7' dimer) | — | |
| | 5187.6 (T2'↔T2' dimer) | — | 2 × S—S inter-molecular linked T2'↔T2' dimer (trace) |
| | 4721.2 (T9'↔T9' dimer) | 4721.9 | 2 × S—S inter-molecular linked T9'↔T9' dimer |
| | 6652.6 (T7'↔T2'↔T9' trimer) | — | |

Example 5

Confirming the Localization of the Disulfide Bridge Between T2 and T4

As the results of Example 4 strongly hint for a disulfide bridge between the aa 229 and 238 another peptide was analyzed. This peptide, IGP 1629 (Ac-PCVRENNS-SkCWVALTPTLA-NH$_2$; SEQ ID NO:13; Ac=acetyl) represents part of the sequence of the monomeric E1 as produced in example 1 and contains the two cysteines potentially linking T2 and T4. The MALDI-TOF-MS spectrum of the acidic stock solution (10% acetic acid, 10% DMSO and 20% acetonitrile/0.1% TFA) of this peptide was analyzed. Surprisingly this stock solution contained mainly a peptide with a disulfide bridge. The oxidizing ability of sulfoxides, e.g., DMSO is often used as an oxidant aid for peptide cyclisation by intramolecular disulfide bridge formation. Sulfoxides are mostly used in combination with buffers at neutral or slightly higher pH; in close contact with air; at peptide concentrations ≦0.25 mg/mL; overnight incubation and often with addition of stronger oxidants.

Based on this experience, it is concluded that the peptide IGP 1629 has the intrinsic ability to form intramolecular disulfide bridges. The peptide contains probably one or two cysteine residues with a low pKa value, making it possible to create preferentially the cyclic peptide (intramolecular disulfide bridge) at this low pH and even at high peptide concentrations of the stock solution (~=1 mg/mL). In itself, this high peptide concentration, without significant dimer- or oligomerisation, is a clear indication that the sequences (and peptide conformation) are favorable to the formation of the cyclic monomer structures and confirmed the presence of a disulfide bridge already in the acidic stock solution. This finding further adds to the data generated in the previous Examples linking peptide T2 with T4 with a disulfide bridge between amino acids 229 and 238. The intramolecular disulfide bridges in the E1s (and thus E1 as E1s comprises all eight cysteines) protein as determined in this and previous Examples are schematically summarized in FIG. 1.

Example 6

Mutation of Cysteine Residues 304 and 306 of E1

The cysteine residues at relative amino acid positions 304 and 306 of E1s are mutated by point mutagenesis to serine or alanine and this E1s protein is expressed as C-terminal (His)$_6$-tagged protein [E1s-C304>S-C306>S-(His)$_6$, or E1s-C304>A-C306>A-(His)$_6$] in *Hansenula polymorpha* as described in Example 1. Cell lysates of these cultures are compared to cell lysates of E1s-(His)$_6$-expressing cultures by western-blot using a monoclonal antibody directed against E1s (IGH201). The increased content of monomeric E1 in the cultures containing E1 with mutation allows to purify large quantities of E1 comprising specific disulfide bridges.

Example 7

Antibodies with Higher Affinity for Monomeric than Sulphonated E1

The monoclonal antibodies directed against E1 and used in this example were generated in two different experiments.
1. The monoclonal antibody IGH 201 is derived from a Balb/c mouse immunized with irreversibly blocked E1 as described in Examples 1 and 2 of WO99/50301. The hybridoma cell line secreting this antibody has been deposited as described in Example 1 herein.
2. The monoclonal antibody IC4 and its subclone, IGH 388, have been derived from an HCV infected individual testing positive for E1 antibodies. The antibody was generated based on the method as described in Example 6 of WO99/60846, with some minor modifications.
   Immune-deficient NOD/ItSz-Prkdc$^{scid}$/Prkdc$^{scid}$ (NOD/SCID) mice were bred under sterile conditions and fed ad libitum with autoclaved food and water without addition of prophylactic antibiotics and used between 8 and 12 weeks of age. Mice were pretreated by sublethal total body irradiation (3 Gy), administered using a linear accelerator, and by intraperitoneal injection of 1 mg purified TMbetal in 500 μl phosphate buffered saline (PBS). TMbeta1 is a rat monoclonal antibody (Ab) directed against the murine IL2 receptor beta chain used for in vivo depletion of mouse natural killer cell activity.

Heparinised venous blood was drawn from a patient with chronic hepatitis C virus (HCV) infection. The patient was serologically negative for hepatitis B virus or human immunodeficiency virus infection. The patient was infected with HCV genotype 1b as determined by INNO-LiPA HCV II (INNOGENETICS, Ghent Belgium) and its serum showed positive reactivity in the INNO-TEST HCV Ab III assay (Abs present directed towards Core, NS3, NS4 and NS5) and an HCV E1 ELISA test. HCV RNA was detectable in the serum using the Amplicor assay (Roche Diagnostics).Values of serum alanine transaminase (ALT) were elevated for 6 month at least two times above the normal values. The patient has not been treated yet with Interferon, Ribavirin or other anti-viral agents.

Human peripheral blood lymphocytes (Hu-PBL) were isolated from the heparinised venous blood by Ficoll-Hypaque (Nycomed, Oslo, Norway) centrifugation. For intrasplenic engraftment in NOD/SCID mice, animals were anesthetized and a subcostal incision of the skin was made followed by incisions of the abdominal wall and the peritoneum. The spleen was carefully exposed and injected with 50 μl of cell suspension in PBS containing $2 \times 10^7$ Hu-PBL. After injection, the spleen was repositioned in the abdominal cavity, and the abdominal wall and skin were sutured separately.

Recombinant hepatitis C envelope protein E1, produced via Vaccinia-infected mammalian cell culture system as described in Examples 1-3 and 5 of WO96/04385 and adjuvanted with Complete Freunds Adjuvant (CFA), was injected subcutaneously in the hind leg of NOD/SCID mice a few hours after Hu-PBL transfer.

Seven days after intrasplenic engraftment, a Hu-PBL-NOD/SCID spleen cell suspension was prepared by gently squeezing the tissue with angled forceps followed by filtration on a sterile gauze to remove larger fragments. Spleen cell suspension consisted for more than 75% of human B lymphocytes. For cell fusion, Hu-PBL-NOD/SCID spleen cells and K6H6/B5 heteromyeloma cells, washed in PBS, were mixed at 5:1 ratio. Polyethylene glycol 1500 (50%; Boehringer Mannheim, Mannheim, Germany) was added for 2 minutes and washed away. Fused cells ($10^5$ per microculture well) were cultured in 200 μl of RPMI 1640 culture medium supplemented with sodium pyruvate (1 mM), L-glutamine (2 mM), 2-ME ($5 \times 10-5$ M), penicillin (100 U/ml), streptomycin (100 μg/ml), non-essential amino acids, hypoxantine-aminopterin-thymidine (all from Life technologies, Paisley, UK), 10% Fetal Clone I serum (Hyclone, Logan, Utah), human recombinant insulin (10 μg/ml; Boehringher Mannheim), ouabain (1 μM, Sigma, St. Louis, Mo.) and 10% BM condimed HI (Boehringher Mannheim).

The in vitro anti-HCV envelope 1 Ab production by the hybridoma cells was evaluated 10 to 14 days after initiation of culture using an HCV E1 ELISA. One mothercolony 1C4 showed strong reactivity and was subcloned until a monoclonal hybridoma cell line was obtained that showed high and stable production of anti-E1 Abs: 1C4/3F3/1A3/6B12. The hybridoma cell line, also referred to as IGH 388, has been deposited in accordance with the Budapest Treaty on Sep. 13, 2000 at the DSMZ (Deutsche Sammlung von Mikroorganismen und Zellkulturen GmbH, Mascheroder Weg 1b, D-38124 Braunschweig, Germany) under accession number DSM ACC2470.

The monoclonal Ab produced by the hybridoma IGH 388, is of the IgG1 isotype and contains a kappa light chain. The VH and VL chain were sequenced and the nucleic acid and amino acid sequences of the variable domains is shown in FIG. 4.

Both these monoclonal antibodies were tested in a dilution series for their reactivity with the sulphonated or monomeric E1 in ELISA. Both the monomeric and sulphonated E1 were presented as a VLP, prepared as described in Example 1 and in WO 02/085932. The results are shown in FIG. 5. Remarkably, a large difference in reactivity was noted with the IGH 388 monoclonal if tested on monomeric versus sulphonated E1 while no such difference was noted for the antibody IGH 201. This clearly indicates that IGH 388 which has been generated as a consequence of natural infection and thus been induced by natural E1, does preferentially recognize an E1 in which disulfide bridges over an E1 without disulfide bridges. Alternatively the antibody IGH 201 which has been generated in mice using an E1 in which at least part of the cysteines were irreversibly blocked does recognize both types of E1 with very similar affinity.

Example 8

Epitope Mapping of IGH 388

The epitope of IGH201 was already known from WO 99/50301 (Example 4). This antibody reacts with the peptides V1V2 (IGP 888, NH$_2$-YEVRNVSGIYHVTNDCSNS-SIVYEAADMIMHTPGC-GGK(biotin)-CONH$_2$; SEQ ID NO:14) and V2V3 (IGP 1036 acetyl-IVYEAADMIMHT-PGCVPCVRENNSSRCWV-GK(biotin)GG; SEQ ID NO:15) of E1 which have the amino acid region 212-226 in common. This region (IYEAADMIMHTPGC; SEQ ID NO:16) contains only one cysteine, which is located at the C-terminal end and is thus not expected to be crucial for the binding of the antibody.

The antibody IGH 388 was similarly tested on a series of E1 peptides and was found to react both with V2V3 (IGP 1036) and V3V4' (IGP 1087, acetyl-PCVRENNSS-RCWVALTPTLAARNASVPTTTIRRHVD -K(biotin)-CONH$_2$; SEQ ID NO:17) of E1 which have the amino acid region 228-240 (PCVRENNSSRCWV; SEQ ID NO:18) in common. This region contains two cysteines which were found to form a disulfide bridge as described in the examples 2-4.

Peptide equivalents of this common region were generated from a various number of HCV genotypes and tested in ELISA for reactivity with IGH 388. Good recognition was seen for at least 70% of the HCV genotypes tested, confirming that the epitope recognized by IGH 388 is located in the region 228-240.

REFERENCES

1. Barton, G. M. & Medzhitov, R. Toll-like receptors and their ligands. *Curr. Top. Microbiol. Immunol* 270, 81-92 (2002).
2. Byl, B. et al. OM197-MP-AC induces the maturation of human dendritic cells and promotes a primary T cell response. *Int Immunopharmacol.* 3, 417-425 (2003).
3. Duchosal, M. A. et al. Immunization of hu-PBL-SCID mice and the rescue of human monoclonal Fab fragments through combinatorial libraries. *Nature* 355, 258-262 (1992).

4. Garry, R. F. & Dash, S. Proteomics computational analyses suggest that hepatitis C virus E1 and pestivirus E2 envelope glycoproteins are truncated class II fusion proteins. *Virology* 307, 255-265 (2003).
5. Grakoui, A., Wychowski, C., Lin, C., Feinstone, S. M. & Rice, C. M. Expression and identification of hepatitis C virus polyprotein cleavage products. *J. Virol.* 67, 1385-1395 (1993).
6. Johnson, D. A. et al. Synthesis and biological evaluation of a new class of vaccine adjuvants: aminoalkyl glucosaminide 4-phosphates (AGPs). *Bioorg. Med. Chem Lett* 9, 2273-2278 (1999).
7. Lapko, V. N., Smith, D. L. & Smith, J. B. Identification of an artifact in the mass spectrometry of proteins derivatized with iodoacetamide. *J Mass Spectrom.* 35, 572-575 (2000).
8. Lauer, G. M. & Walker, B. D. Hepatitis C virus infection. *N. Engl J. Med.* 345, 41-52 (2001).
9. Merola, M. et al. Folding of hepatitis C virus E1 glycoprotein in a cell-free system. *J Virol.* 75, 11205-11217 (2001).
10. Persing, D. et al. Taking toll: lipid A mimetics as adjuvants and immunomodulators. *Trends Microbiol.* 10, S32 (2002).
11. Persson, M. A., Caothien, R. H. & Burton, D. R Generation of diverse high-affinity human monoclonal antibodies by repertoire cloning. *Proc. Natl. Acad. Sci. U.S.A* 88, 2432-2436 (1991).
12. Pohlmann, S. et al. Hepatitis C virus glycoproteins interact with DC-SIGN and DC-SIGNR. *J Virol.* 77, 4070-4080 (2003).
13. Rein, A. et al. Inactivation of murine leukemia virus by compounds that react with the zinc finger in the viral nucleocapsid protein. *J. Virol* 70, 4966-4972 (1996).
14. Riedl, P., Buschle, M., Reimann, J. & Schirmbeck, R. Binding immune-stimulating oligonucleotides to cationic peptides from viral core antigen enhances their potency as adjuvants. *Eur. J. Immunol.* 32, 1709-1716 (2002).
15. Shiffman, M. L. Improvement in liver histopathology associated with interferon therapy in patients with chronic hepatitis C. *Viral Hepatitis Reviews* 5, 27-43 (1999).
16. Shimotohno, K. et al. Processing of the hepatitis C virus precursor protein. *J. Hepatol.* 22, 87-92 (1995).
17. Walewski, J. L., Keller, T. R., Stamp, D. D. & Branch, A. D. Evidence for a new hepatitis C virus antigen encoded in an overlapping reading frame. *RNA.* 7, 710-721 (2001).
18. Winter, G. & Harris, W. J. Humanized antibodies. *Immunol. Today* 14, 243-246 (1993).
19. Xu, Z. et al. Synthesis of a novel hepatitis C virus protein by ribosomal frameshift. *EMBO J.* 20, 3840-3848 (2001).

---

The invention claimed is:

1. An isolated recombinant or synthetic HCV E1 envelope protein or a part thereof comprising at least one of the following disulfides:

a disulfide between the pair of cysteines at amino acid positions 207 and 226, a disulfide between the pair of cysteines at amino acid positions 229 and 238, or a disulfide between the pair of cysteines at amino acid positions 272 and 281, wherein said amino acid positions are relative to the HCV polyprotein which is starting with the methionine of the Core protein at amino acid position 1 of said HCV polyprotein.

2. The HCV E1 envelope protein or a part thereof according to claim 1 further comprising at least one of the cysteines at amino acid positions 304 or 306 wherein said at least one cysteine is carrying a free thiol group or a thiol group which is blocked.

3. The HCV E1 envelope protein or a part thereof according to claim 2 wherein said blocked thiol group is reversibly or irreversibly blocked.

4. A viral-like particle comprising the HCV E1 envelope protein or part thereof according to any one of claims 1 to 3.

5. A composition comprising the HCV E1 envelope protein or part thereof according to any one of claims 1 to 3 or a viral-like particle comprising the HCV E1 envelope protein or part thereof, and at least one of a pharmaceutically acceptable carrier, adjuvant or vehicle.

6. An immunogenic composition comprising the HCV E1 envelope protein or part thereof according to any one of claims 1 to 3 or the viral-like particle -comprising the HCV E1 envelope protein or part thereof, and at least one of a pharmaceutically acceptable carrier, adjuvant or vehicle.

7. An isolated protein comprising the HCV E1 envelope protein or part thereof according to any of claims 1 to 3.

8. The isolated protein according to claim 7 further comprising at least one of:
- an N-terminal flanking amino acid or amino acid sequence of an HCV protein or part thereof not naturally contiguous with said HCV E1 envelope protein or part thereof;
- a C-terminal flanking amino acid or amino acid sequence of an HCV protein or part thereof not naturally contiguous with said HCV E1 envelope protein or part thereof;
- an N-terminal flanking non-HCV amino acid or amino acid sequence;
- a C-terminal flanking non-HCV amino acid or amino acid sequence.

9. The isolated protein according to claim 7 comprising the HCV E1 envelope protein or part thereof as carrier protein.

* * * * *

UNITED STATES PATENT AND TRADEMARK OFFICE
CERTIFICATE OF CORRECTION

PATENT NO. : 7,413,741 B2  Page 1 of 1
APPLICATION NO. : 11/073942
DATED : August 19, 2008
INVENTOR(S) : Depraetere et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 736 days Delete the phrase "by 736 days" and insert -- by 186 days --

Signed and Sealed this

Twenty-third Day of December, 2008

JON W. DUDAS
*Director of the United States Patent and Trademark Office*